(12) United States Patent
Yoshida et al.

(10) Patent No.: US 8,940,946 B2
(45) Date of Patent: Jan. 27, 2015

(54) METHOD FOR PRODUCING HIGH-PURITY 1,5-PENTANEDIOL

(71) Applicant: Ube Industries, Ltd., Ube-shi (JP)

(72) Inventors: Yasutaka Yoshida, Ube (JP); Kenji Hirotsu, Ube (JP); Ryo Fujimoto, Ube (JP); Ryousuke Katsura, Ube (JP); Satoru Fujitsu, Ube (JP); Takashi Doi, Ube (JP); Kouichi Kashiwagi, Ube (JP)

(73) Assignee: Ube Industries, Ltd., Ube-shi (JP)

( * ) Notice: Subject to any disclaimer, the term of this patent is extended or adjusted under 35 U.S.C. 154(b) by 0 days.

(21) Appl. No.: 14/356,773

(22) PCT Filed: Nov. 19, 2012

(86) PCT No.: PCT/JP2012/079999
§ 371 (c)(1),
(2) Date: May 7, 2014

(87) PCT Pub. No.: WO2013/073705
PCT Pub. Date: May 23, 2013

(65) Prior Publication Data
US 2014/0309461 A1      Oct. 16, 2014

(30) Foreign Application Priority Data
Nov. 18, 2011   (JP) .................. 2011-252341

(51) Int. Cl.
*C07C 29/132*   (2006.01)
*C07C 31/20*    (2006.01)
*C07C 29/84*    (2006.01)

(52) U.S. Cl.
CPC .............. *C07C 29/132* (2013.01); *C07C 29/84* (2013.01)
USPC ........................... 568/865; 568/866; 568/867

(58) Field of Classification Search
USPC ........................ 568/865, 866, 867
See application file for complete search history.

(56) References Cited

U.S. PATENT DOCUMENTS 2,768,978 A      10/1956   Robertson

FOREIGN PATENT DOCUMENTS

| DE | 918 325      | 9/1954  |
| GB | 627293       | 8/1949  |
| JP | 7 232067     | 9/1995  |
| JP | 2001 316311  | 11/2001 |
| JP | 2009 046417  | 3/2009  |
| WO | 97 31882     | 9/1997  |

OTHER PUBLICATIONS

"Organic Synthesis Coll." vol. 3, p. 693(1995); vol. 26, p. 83 (1946).
International Search Report Issued Jan. 8, 2013 in PCT/JP12/079999 Filed Nov. 19, 2012.

*Primary Examiner* — Brian J Davis
(74) *Attorney, Agent, or Firm* — Oblon, Spivak, McClelland, Maier & Neustadt, L.L.P.

(57) ABSTRACT

The present invention has an object to provide a method for efficiently producing high-purity 1,5-pentanediol by reacting tetrahydrofurfuryl alcohol with hydrogen. This manufacturing method for producing high-purity 1,5-pentanediol comprises: step (I): a step of obtaining a crude reaction product by a hydrogenolysis reaction of tetrahydrofurfuryl alcohol with hydrogen carried out in the presence of a copper-containing catalyst with reaction temperature of 200 to 350° C. and reaction pressure of 1 to 40 MPa until conversion rate of tetrahydrofurfuryl alcohol reaches 80% or less; step (II): a step of separating tetrahydrofurfuryl alcohol and crude 1,5-pentanediol (A) from the crude reaction product obtained in the step (I), and then, supplying recovered tetrahydrofurfuryl alcohol as a raw material for the step (I); and step (III): a step of obtaining the high-purity 1,5-pentanediol by distillation of the crude 1,5-pentanediol (A) obtained in the step (II).

11 Claims, 3 Drawing Sheets

US 8,940,946 B2

METHOD FOR PRODUCING HIGH-PURITY 1,5-PENTANEDIOL

TECHNICAL FIELD

The present invention relates to a method for producing high-purity 1,5-pentanediol by convenient operation with an industrially low cost, a high reaction selectivity, and a superior productivity by using tetrahydrofurfuryl alcohol as a manufacturing raw material thereof.

For example, tetrahydrofurfuryl alcohol used in the present invention is one of the so-called biomass raw materials; and 1,5-pentanediol produced by using these as manufacturing raw materials thereof is useful as a raw material (monomer) for polymers such as a polyester, a polycarbonate, and a polyurethane, and as a raw material for a pharmaceutical drug and an agricultural chemical, an additive for a resin, a solvent for detergent, and the like.

BACKGROUND ART

In the past, to produce 1,5-pentanediol, a method is well known in which a carboxylic acid mixture raw material including glutaric acid, adipic acid, 6-hydroxy caproic acid, and so forth which are by-produced during manufacturing of cyclohexanone and/or cyclohexanol by air-oxidation of cyclohexane is esterified, and then they are reduced by hydrogen by using a copper-based catalyst to give 1,5-pentanediol and 1,6-hexanediol, which is then followed by separation by distillation (see, for example, Patent Document 1). As a closely-related method, a method is known in which a mixture of dicarboxylic acids which are by-produced in an adipic acid manufacturing plant is used as the raw material thereof (see, for example, Patent Document 2).

On the other hand, as a method for producing 1,5-pentanediol by using tetrahydrofurfuryl alcohol as the manufacturing raw material thereof, a method for producing 1,5-pentanediol from tetrahydrofurfuryl alcohol in the presence of a copper-chromium type catalyst and a method for producing 1,5-pentanediol from furfural in the presence of a copper-aluminum type catalyst have been reported (see, for example, Patent document 3, Patent Document 4, and Non-Patent Document 1).

Additionally, in recent years, a method for producing an alkylene polyol by using a metal catalyst other than a copper type catalyst has been reported (see, for example, Patent Document 5). In this Patent Document 5, a method is described in which 1,5-pentanediol is obtained as a mixture with ring-opened compounds such as 1,2-pentanediol and 1-pentanol as well as a decomposed product such as 2-methyltetrahydrofuran by using an aqueous solution containing tetrahydrofurfuryl alcohol as the manufacturing raw material thereof in the presence of a copper-containing catalyst supporting rhodium and one or more metal atoms selected from rhenium, molybdenum, and tungsten.

Patent Document 1: International Publication No. WO1997/031882
Patent Document 2: Japanese Patent Laid-Open Publication No. 2001-316311
Patent Document 3: U.S. Pat. No. 2,768,978
Patent Document 4: U.S. Pat. No. 627,293
Patent Document 5: Japanese Patent Laid-Open Publication No. 2009-46417
Non-Patent Document 1: Organic Synthesis Coll. Vol. 3, p. 693 (1955); Vol. 26, p. 83 (1946).

SUMMARY OF THE INVENTION

Problems to be Solved by the Invention

However, for example, in the method described in Patent Document 1, to obtain the high-purity 1,5-pentanediol, separation thereof from 1,6-hexanediol, which is a main product thereof, 1,5-hexanediol and 1,4-cyclohexanediol, which are a by-product having a secondary hydroxy group, is so complicated that this method could not be regarded as an industrially efficient method.

In the method described in Patent Document 3, a good reaction conditions to give the reaction selectivity to the byproduct pentanol of 6% or less could not found also as an industrial method; in addition, there is no disclosure at all as to a specific method for purification of 1,5-pentanediol obtained, a method for recovering a unreacted raw material, reusability of the used catalyst, and purity of 1,5-pentanediol after purification.

In the method described in Non-Patent Document 1, the yield of 1,5-pentanediol is described, but the reaction selectivity thereto is not mentioned in detail; and in addition, for example, there is no disclosure at all as to a specific method for purification of 1,5-pentanediol obtained, a method for recovering a unreacted raw material, reusability of the used catalyst, purity of 1,5-pentanediol after purification, and the like.

In these methods, the unreacted tetrahydrofurfuryl alcohol and the used catalyst are not reused after recovery, thereby giving rise to a process producing very large amount of waste materials, so that these methods are not feasible from viewpoints of economy and environmental friendliness.

Further, in Patent Document 4, a method in which furfural is fed continuously is used; and it is reported that, for example, in the case that the reaction temperature is 120° C., content of 1,5-pentanediol in the product after re-distillation is only about 30% by mass in terms of the mixture thereof with 1,2-pentanediol, and that in the case that the reaction temperature is 150° C., similarly, content of 1,5-pentanediol in the product after re-distillation is only about 30% by mass in terms of the mixture thereof with 1,2-pentanediol, moreover, in which about 30% by mass of 1-pentanol is present (Example 4 in Patent Document 4). Therefore, any of the conventional methods could not be considered as fully satisfactory industrial production methods. In Patent Document 2, it is reported that 1,5-pentanediol contaminated with, for example, a branched chain-like or a cyclic alkanediol having a secondary hydroxy group such as 1,5-hexanediol, 1,4-cyclohexanediol, and 1,2-pentanediol, these compounds being by-products, has bad effects to manufacturing of a polyurethane resin or a polyester resin. Therefore, when considering its use as the manufacturing raw material for industrial resins, especially 1,5-pentanediol containing less amounts of secondary hydroxide-containing diols as impurities is requested.

On the other hand, in the method of Patent Document 5, which is the reaction method using a new metal catalyst containing a metal other than copper such as rhodium, it is disclosed that to satisfactorily achieve both the reaction conversion rate and the reaction selectivity is difficult when the reaction is carried out in a reaction solution not containing water. And thus, an aqueous solution containing low concentration of tetrahydrofurfuryl alcohol is used as the manufacturing raw material thereof; however, use of this low concentration aqueous solution could not be regarded as an economical manufacturing method because of low production efficiency; and moreover, the operation to separate water-soluble 1,5-pentanediol from water after completion of the reaction is complicated, and thus, this method could not be considered as a suitable industrial method either.

Accordingly, the present invention has an object to provide a highly efficient method for producing the high-purity 1,5-pentanediol by reacting tetrahydrofurfuryl alcohol with hydrogen.

Means for Solving the Problems

That is, the present invention relates to the following (1) to (11).

(1) A method for producing high-purity 1,5-pentanediol, comprising:
step (I): a step of obtaining a crude reaction product by a hydrogenolysis reaction of tetrahydrofurfuryl alcohol with hydrogen carried out in the presence of a copper-containing catalyst with reaction temperature of 200 to 350° C. and reaction pressure of 1 to 40 MPa until conversion rate of tetrahydrofurfuryl alcohol reaches 80% or less;
step (II): a step of separating tetrahydrofurfuryl alcohol and crude 1,5-pentanediol (A) from the crude reaction product obtained in the step (I), and then, supplying recovered tetrahydrofurfuryl alcohol as a raw material for the step (I); and
step (III): a step of obtaining the high-purity 1,5-pentanediol by distillation of the crude 1,5-pentanediol (A) obtained in the step (II)
(2) The method for producing high-purity 1,5-pentanediol according to (1), wherein water content contained in the tetrahydrofurfuryl alcohol to be used in the step (I) is 1% or less by mass.
(3) The method for producing high-purity 1,5-pentanediol according to (1) or (2), wherein the copper-containing catalyst after use is recovered by separation after ending of the reaction in the step (I), and then the copper-containing catalyst thereby recovered is reused in the step (I).
(4) The method for producing high-purity 1,5-pentanediol according to any one of (1) to (3), wherein crude 1,5-pentanediol is obtained by removing high-boiling point compounds by distillation from the crude 1,5-pentanediol (A) obtained in the step (II), and then is used in distillation in the step (III).
(5) The method for producing high-purity 1,5-pentanediol according to any one of (1) to (3), wherein a saponification agent is added to the crude reaction product obtained in the step (I), and then the step (II) and the step (III) are carried out successively.
(6) The method for producing high-purity 1,5-pentanediol according to any one of (1) to (3), wherein a saponification agent is added to the crude 1,5-pentanediol (A) obtained in the step (II), and then the step (III) is carried out.
(7) The method for producing high-purity 1,5-pentanediol according to any one of claims 1 to 6, wherein total amount of diol compounds having a secondary hydroxy group contained in 1,5-pentanediol obtained in the step (III) is 1% or less by mole.
(8) The method for producing high-purity 1,5-pentanediol according to any one of (1) to (7), wherein a co-existing atom of the copper-containing catalyst used in the step (I) comprises at least one atom "B" selected from the group consisting of zinc, iron, aluminum, chromium, and silicon.
(9) The method for producing high-purity 1,5-pentanediol according to (8), wherein the copper-containing catalyst to be used in the step (I) is a copper-containing catalyst further comprising, in addition to copper atom and the atom (B), at least one atom "C" selected from the group consisting of barium, calcium, manganese, lanthanum, cerium, and magnesium.

(10) The method for producing high-purity 1,5-pentanediol according to any one of (1) to (9), wherein the tetrahydrofurfuryl alcohol to be used in the step (I) is tetrahydrofurfuryl alcohol synthesized by using furfural as a raw material thereof.
(11) The method for producing high-purity 1,5-pentanediol according to any one of (1) to (10), wherein acid value of the tetrahydrofurfuryl alcohol to be used in the step (I) is 2 mg-KOH/g or less.

Effect of the Invention

According to the production method of the present invention, provided is a method for producing high-purity 1,5-pentanediol by reacting tetrahydrofurfuryl alcohol with hydrogen under a specific condition with a high regioselectivity, which is followed by distillation of the crude reaction product thereby obtained.

Therefore, according to the present invention, provided is a method for producing 1,5-pentanediol contaminated with extremely small amount of various by-products including diols having a secondary hydroxy group such as 1,2-pentanediol, 1,5-hexanediol, and 1,4-cyclohexanediol, as well as an alkyl alcohol such as 1-pentanol, these having been by-produced in conventional production methods. Especially, in the present invention, discovery was made that δ-valerolactone was generated during purification by distillation in the step (II) and/or the step (III) due to depolymerization of a high-boiling point substance mixture containing poly(δ-valerolactone) by-produced in the step (I), and that this δ-valerolactone contaminated the distilled 1,5-pentanediol product, thereby leading difficult purification by distillation to obtain the high-purity 1,5-pentanediol; and therefore, the present invention is also the one which solved this newly discovered problem.

In addition, the production process of the present invention is an extremely economical method (advantageous in terms of cost) which produces very small amounts of waste materials because unreacted tetrahydrofurfuryl alcohol in the reaction of the step (I) is recovered in the step (II), and in addition, the used copper-containing catalyst is recycled for reuse. Further, the present invention provides an environmentally friendly manufacturing method intending a green chemistry because tetrahydrofurfuryl alcohol derived from a biomass may be used also as the manufacturing raw material thereof.

MODES FOR CARRYING OUT THE INVENTION

Figure 1:
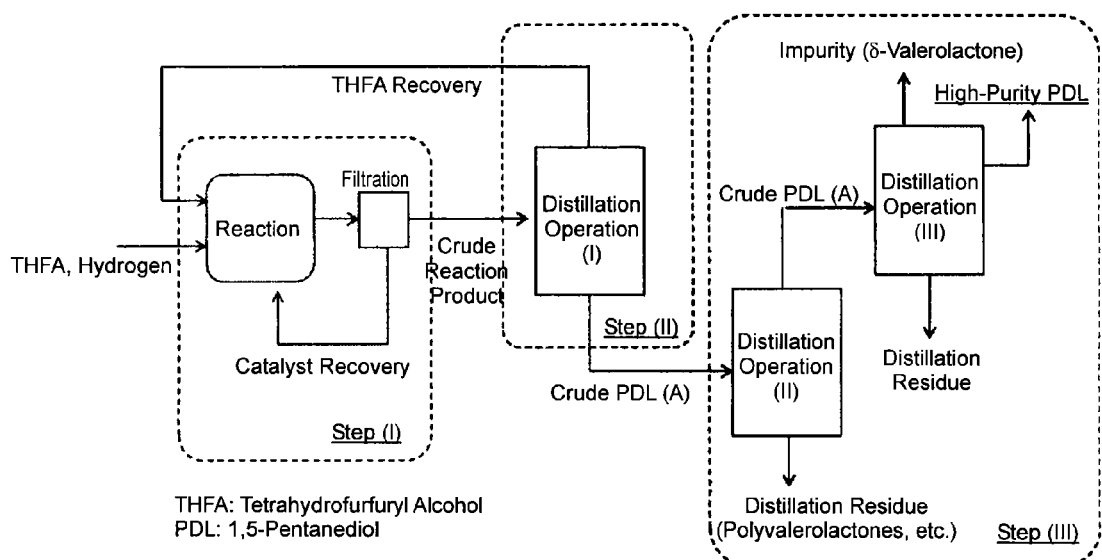
FIG. 1 shows an example of the operation of the method for producing 1,5-pentanediol of the present invention in which saponification operation is not carried out. Meanwhile, the respective parts enclosed by the dotted lines briefly describe operations in each step.

The method for producing 1,5-pentanediol of the present invention is the method comprises following steps (I) to (III):

step (I): a step of obtaining a crude reaction product by a hydrogenolysis reaction of tetrahydrofurfuryl alcohol with hydrogen carried out in the presence of a copper-containing catalyst with reaction temperature of 200 to 350° C. and reaction pressure of 1 to 40 MPa until conversion rate of tetrahydrofurfuryl alcohol reaches 80% or less;

step (II): a step of separating tetrahydrofurfuryl alcohol and crude 1,5-pentanediol (A) from the crude reaction product obtained in the step (I), and then, supplying recovered tetrahydrofurfuryl alcohol as a raw material for the step (I); and step (III): a step of obtaining the high-purity 1,5-pentanediol by distillation of the crude 1,5-pentanediol (A) obtained in the step (II)

Step (I)

Step (I) of the present invention is the step of obtaining a crude reaction product by a hydrogenolysis reaction of tetrahydrofurfuryl alcohol with hydrogen carried out in the presence of a copper-containing catalyst with reaction temperature of 200 to 350° C. and reaction pressure of 1 to 40 MPa until conversion rate of tetrahydrofurfuryl alcohol reaches 80% or less <Raw Material: Tetrahydrofurfuryl Alcohol>

As to tetrahydrofurfuryl alcohol used as the manufacturing raw material in the production method of the present invention, a commercially available compound thereof may be used as it is, or after it is further purified; and thus, any of them may be used. For example, a method is known in which furfural is produced from raw materials derived from agricultural products such as corncob, sugarcane bagasse, and wood powder, and then, this furfural is hydrogenated to give furfuryl alcohol (Japanese Patent Laid-Open Publication No. H07-232067), and thereafter, when this furfuryl alcohol is hydrogenated by using a catalyst such as Pd/C, tetrahydrofurfuryl alcohol can be obtained. Therefore, to use tetrahydrofurfuryl alcohol derived from the biomass like this is preferable in view of the green chemistry.

Water content contained in tetrahydrofurfuryl alcohol to be used in the step (I) is, in order to prevent deterioration of its reactivity, preferably 3% or less by mass, more preferably 1% or less by mass, or particularly preferably 0.5% or less by mass. Because contamination by an acid component also causes deterioration of the reactivity, acid value of tetrahydrofurfuryl alcohol is preferably 3 mg-KOH/g or less, more preferably 2 mg-KOH/g or less, or particularly preferably 1 mg-KOH/g or less.

In addition, in the present invention, all or part of tetrahydrofurfuryl alcohol recovered in the later-mentioned step (II) (hereinafter, sometimes this is referred to as "recovered THFA") is reused in the step (I). When this is reused, use amount of the recovered THFA is in the range of more than 0% by mass to 100% or less by mass relative to the total amount of tetrahydrofurfuryl alcohol to be used in the step (I).

<Copper-Containing Catalyst>

It is preferable that the copper-containing catalyst used in the present invention contain copper atom and at least one co-existing atom selected from the group consisting of the elements of the third to the sixth periods of the II to XIV groups in the periodical table and lanthanide elements. It is preferable that this co-existing atom includes at least one metal atom selected from the group consisting of the atoms "B" and the atoms "C" shown below. Here, the co-existing atoms mean the atoms to constitute the metal catalyst together with copper atom contained in the metal catalyst.

The copper-containing catalyst used in the present invention includes a supported copper-containing catalyst in which copper atom and co-existing atoms are supported on a later-mentioned carrier. Moreover, in the reaction of the present invention, the copper-containing catalyst may be used solely or as a mixture of two or more kinds of it.

In the copper-containing catalyst used in the reaction of present invention, mass ratio of the copper atom to the co-existing atom (copper atom/co-existing atom) is not particularly limited; however, usually in the range of 0.1/99.9 to 99.9/0.1, preferably in the range of 1/99 to 99/1, or more preferably in the range of 5/95 to 95/5, in order to enhance the reaction selectivity to 1,5-pentanediol of the present invention. Here, the said mass ratio is the content ratio of the metal atoms in the copper-containing catalyst.

Atom "B":

As to the co-existing atom "B" of the present invention, used is at least one metal atom selected from the group consisting of magnesium (Mg), calcium (Ca), barium (Ba), lanthanum (La), cerium (Ce), titanium (Ti), zirconium (Zr), vanadium (V), niobium (Nb), chromium (Cr), molybdenum (Mo), tungsten (W), manganese (Mn), rhenium (Re), iron (Fe), cobalt (Co), osmium (Os), zinc (Zn), aluminum (Al), gallium (Ga), indium (In), tin (Sn), and silicon (Si). Meanwhile, among these atoms "B", in order to obtain 1,5-pentanedil with a high reaction selectivity thereto, at least one atom selected from the group consisting of zinc, iron, aluminum, chromium, and silicon is preferable; while at least one atom selected from the group consisting of zinc, aluminum, chromium, and silicon is more preferable, though zinc or chromium is further preferably used.

Accordingly, in the reaction of the present invention, for example, in order to obtain 1,5-pentanediol with a high reaction electivity thereto, the mass ratio of the copper atom to the atom "B" (copper atom/atom "B") in the copper-containing catalyst to be used therein is usually in the range of 10/90 to 99/1, more preferably in the range of 20/80 to 99/1, still more preferably in the range of 30/70 to 95/5, further still more preferably in the range of 40/60 to 95/5, or particularly preferably in the range of 45/55 to 90/10. Here, the said mass ratio is the content ratio of the metal atoms in the copper-containing catalyst.

Atom "C":

The copper-containing catalyst used in the present invention may further contain as the co-existing atom, in addition to the foregoing atom "B", at least one atom "C" selected from the group consisting of aluminum (Al), barium (Ba), calcium (Ca), manganese (Mn), iron (Fe), nickel (Ni), magnesium (Mg), lanthanum (La), zirconium (Zr), cerium (Ce), and cobalt (Co). However, the atom "C" shall be selected from different atoms other than the atoms "B". Here, as to the atom "C", at least one co-existing atom selected from the group consisting of aluminum (Al), barium (Ba), calcium (Ca), manganese (Mn), lanthanum (La), and magnesium (Mg) is preferable. Among them, in order to obtain a high reaction selectivity, a combination of copper atom, zinc atom, and atom "C", a combination of copper atom, chromium atom, and atom "C", or a combination of copper atom, silicon atom, and atom "C" is especially preferable. Accordingly, by using a copper-containing catalyst further containing atom "C", i.e., if a copper-containing catalyst containing copper atom, atom "B", and atom "C", is used in the reaction of the present invention, 1,5-pentanediol having the hydroxy groups at the both molecular terminals thereof can be obtained with a further higher reaction selectivity thereto.

Accordingly, in the reaction of the present invention, in order to obtain 1,5-pentanediol having hydroxy groups at both molecular terminals thereof with a high reaction selectivity thereto, for example, content of the atom "C" is, as the mass ratio of the copper atom and the atom "B" to the atom "C" in the copper-containing catalyst to be used therein (sum of copper atom and atom "B"/atom "C"), usually in the range of 10/90 to 99/1, preferably in the range of 30/70 to 95/5, more preferably in the range of 40/60 to 95/5, or particularly preferably in the range of 45/55 to 95/5. Here, the said mass ratio is the content ratio of the metal atoms in the copper-containing catalyst.

Supported Copper-Containing Catalyst:

The copper-containing catalyst of the present invention includes a supported copper-containing catalyst in which metal atoms containing the foregoing copper atom and co-existing atoms are supported on a carrier.

In the supported copper-containing catalyst of the present invention, the carrier thereof is not particularly limited; however, preferably used is at least one carrier selected from the group consisting of zinc oxide, silica, alumina, chromia, silica alumina (aluminosilicate), ceria, magnesia, calcia, titania, silica titania (titanosilicate), zirconia, active carbon, zeolite, and mesoporous material (mesoporous alumina, mesoporous silica, mesoporous carbon). Moreover, the foregoing carrier is preferably porous in view of the reaction efficiency.

Content of copper atom (Cu) in the supported copper-containing catalyst of the present invention is preferably in the range of 0.1 to 99.9% by mass, more preferably in the range of 1 to 90% by mass, still more preferably in the range of 5 to 80% by mass, or particularly preferably in the range of 10 to 80% by mass.

From the foregoing discussion, as the copper-containing catalyst to be used in the present invention;
a copper-containing catalyst containing copper atom and at least one atom "B" selected from the group consisting of magnesium (Mg), calcium (Ca), barium (Ba), lanthanum (La), cerium (Ce), titanium (Ti), zirconium (Zr), vanadium (V), niobium (Nb), molybdenum (Mo), tungsten (W), manganese (Mn), rhenium (Re), iron (Fe), cobalt (Co), osmium (Os), zinc (Zn), aluminum (Al), gallium (Ga), indium (In), tin (Sn), chromium (Cr), and silicon (Si); or a supported copper-containing catalyst containing these metals supported on one carrier selected from the group consisting of zinc oxide, silica, alumina, titania, zirconia, and activated carbon, are preferred;
a copper-containing catalyst containing copper atom, zinc atom or chromium atom, and at least one atom "C" selected from the group consisting of barium (Ba), calcium (Ca), manganese (Mn), iron (Fe), lanthanum (La), chromium (Cr), and magnesium (Mg); or a copper-containing catalyst containing copper atom, chromium atom, and at least one atom "C" selected from the group consisting of barium (Ba) and manganese (Mn); or a supported copper-containing catalyst containing these metals supported on one carrier selected from the group consisting of zinc oxide, silica, alumina, titania, zirconia, and activated carbon are more preferred;
a copper-containing catalyst selected from the group consisting of a copper-zinc type metal catalyst, a copper-zinc-aluminum type metal catalyst, a copper-zinc-iron type metal catalyst, a copper-zinc-silicon type metal catalyst, a copper-zinc-barium type metal catalyst, a copper-zinc-calcium type metal catalyst, a copper-zinc-manganese type metal catalyst, a copper-zinc-manganese-barium type metal catalyst, a copper-zinc-lanthanum type metal catalyst, a copper-zinc-barium-manganese-lanthanum type metal catalyst, a copper-zinc-cerium type metal catalyst, a copper-zinc-magnesium type metal catalyst, a copper-aluminum type metal catalyst, a copper-aluminum-iron type metal catalyst, a copper-aluminum-silicon type metal catalyst, a copper-aluminum-barium type metal catalyst, a copper-aluminum-calcium type metal catalyst, a copper-aluminum-manganese type metal catalyst, a copper-aluminum-manganese-barium type metal catalyst, a copper-aluminum-lanthanum type metal catalyst, a copper-aluminum-lanthanum-barium type metal catalyst, a copper-aluminum-cerium type metal catalyst, a copper-aluminum-magnesium type metal catalyst, a copper-silicon type metal catalyst, a copper-silicon-iron type metal catalyst, a copper-silicon-aluminum type metal catalyst, a copper-silicon-barium type metal catalyst, a copper-silicon-calcium type metal catalyst, a copper-silicon-manganese type metal catalyst, a copper-silicon-manganese-barium type metal catalyst, a copper-silicon-lanthanum type metal catalyst, a copper-silicon-lanthanum-barium type metal catalyst, a copper-silicon-cerium type metal catalyst, a copper-silicon-magnesium type metal catalyst, a copper-chromium type metal catalyst, a copper-chromium-aluminum type metal catalyst, a copper-chromium-silicon type metal catalyst, a copper-chromium-barium type metal catalyst, a copper-chromium-calcium type metal catalyst, a copper-chromium-manganese type metal catalyst, a copper-chromium-manganese-barium type metal catalyst, a copper-chromium-lanthanum type metal catalyst, a copper-chromium-lanthanum-barium type metal catalyst, a copper-chromium-cerium type metal catalyst, and a copper-chromium-magnesium type metal catalyst is still more preferred.

Meanwhile, the above-mentioned metal catalysts are preferably oxides or carbonate salts which contain copper atom and co-existing atoms (atom "B", and atom "B" and further atom "C"). For example, the above-mentioned copper-zinc-barium type metal catalysts are preferably oxides which contain copper atom, zinc atom, and barium atom, or carbonate salts which contain the same atoms. Meanwhile, the copper-containing catalyst to be used in the present invention includes the foregoing metal catalysts that are treated under a reducing atmosphere such as, for example, hydrogen and carbon monoxide.

Specific Surface Area of the Copper-Containing Catalyst:

Specific surface area of the copper-containing catalyst or of the supported copper-containing catalyst of the present invention is preferably in the range of 1 to 1000 m$^2$/g, more preferably in the range of 5 to 500 m$^2$/g, or particularly preferably in the range of 5 to 300 m$^2$/g.

The average pore diameter of the carrier is preferably in the range of 10 to 500 Å, or more preferably in the range of 100 to 250 Å. Meanwhile, the specific surface area of the copper-containing catalyst of the present invention is measured by the BET method; and the average pore diameter thereof is measured by the mercury intrusion method. Particle size of the copper-containing catalyst of the present invention is not particularly limited. The copper-containing catalysts of the present invention that are commercially available may be used as they are, provided that copper-containing catalysts satisfy the above ranges; or alternatively, they may be obtained by adjusting the composition ratio of copper atom to other metal atoms by a heretofore known method.

Method for Preparing the Copper-Containing Catalysts:

The copper-containing catalysts of the present invention may be prepared, for example, as follows: firstly, a catalyst precursor comprising copper and zinc is precipitated by the co-precipitation method in the liquid phase, and then, the obtained precipitates are washed, dried, and then calcined, as described in Reference Examples 1 to 3 of the present invention, or the like.

On the other hand, the supported copper-containing catalysts of the present invention may be used as they are if they are commercially available. They may be also prepared by the method, for example, as following; water is removed from an impregnated mixture of an aqueous solution or slurry containing: at least one copper compound selected from the group consisting of copper, copper oxide, copper iodide, copper bromide, copper chloride, copper fluoride, copper sulfate, copper nitrate, copper salts of organic sulfonic acids such as copper methanesulfonate salt and copper trifluoromethanesulfonate salt; an aqueous solution or slurry containing at least one selected from the group consisting of oxides, iodides, bromides, chlorides, fluorides, sulfate salts, nitrate salts and organic sulfonic acids such as methanesulfonate salt and trifluoromethanesulfonate salt of at least one co-existing atom "B" and/or atom "C" selected from the elements of the third to the sixth periods of the II to XIV groups and lanthanide elements in the periodical table; and a carrier; and then, the solid thereby obtained is calcined. Meanwhile, use amounts of the copper compounds and the metal compounds containing other metal atoms may be adjusted appropriately in accordance with the objective blending ratios. As to water to be used for preparation of the aqueous solution of the copper compounds, for example, pure water, ultrapure water, ion-exchanged water, or the like may be used, wherein use amount thereof is not particularly limited.

Preparation method of the supported copper-containing catalyst of the present invention is different depending on the kind and the like of the copper compound and/or the other metal compounds to be used; for example, the said catalyst may be obtained with the preparation time of 0.1 to 20 hours and by evaporating water from the aqueous solution or the slurry mentioned before. The burning temperature is preferably in the range of −5 to 800° C., or more preferably in the range of 100 to 500° C.

Use Amount of the Copper-Containing Catalyst:

In the reaction of the present invention, each of the copper-containing catalysts of the present invention may be used solely or as a mixture of two or more of them; or alternatively, the catalyst containing copper atom and other metal atoms and the supported metal catalyst may be used together. In the case when the reaction style (reaction system) is a liquid phase slurry reaction, use amount (total) of the metal catalyst is preferably in the range of 0.01 to 50% by mass, more preferably in the range of 0.01 to 20% by mass, still more preferably in the range of 0.05 to 10% by mass, or particularly preferably in the range of 0.1 to 5% by mass, relative to tetrahydrofurfuryl alcohol. In the case when the reaction style (reaction system) is a fixed-bed flow reaction, use amount of the metal catalyst and feed amount of tetrahydrofurfuryl alcohol are controlled such that the space time yield (STY) may become in the range of 1 to 5000 g/liter-hour, preferably in the range of 10 to 1000 g/liter-hour, or more preferably in the range of 50 to 500 g/liter-hour. Within the above ranges, 1,5-pentanediol can be obtained with a high reaction selectivity thereto and with a higher yield.

Hydrogen to be Used in the Present Invention

The method for producing 1,5-pentanediol of the present invention is carried out by using hydrogen. Amount of hydrogen to be used is not particularly limited provided that the amount thereof (mole) is equivalent or more in terms of mole relative to tetrahydrofurfuryl alcohol. Meanwhile, it is preferable that the reaction of the present invention be carried out under a hydrogen gas atmosphere (under the hydrogen pressure), wherein the hydrogen pressure thereat is preferably in the range of an atmospheric pressure to 50 MPa, more preferably in the range of 1 to 40 MPa, still more preferably in the range of 10 to 38 MPa, or particularly preferably in the range of 15 to 35 MPa. Excess hydrogen remained after the reaction may also be recycled to the step (I) and then reused.

Reaction Solvent

In the production method of the present invention, a reaction solvent may be used, for example, in order to adjust dispersion of the copper-containing catalyst or to increase solubility of tetrahydrofurfuryl alcohol and/or the product 1,5-pentanediol; however, in the present invention, it is preferable that the reaction be carried out without using a reaction solvent.

Kind of the Reaction Solvent:

However, in the case that the reaction solvent is necessary, Example of the reaction solvent to be used includes alcohols such as methanol, ethanol, 1-propanol, 2-propanol, n-butanol, t-butanol, and ethylene glycol; hydrocarbons such as heptane, hexane, cyclohexane, benzene, and toluene; amides such as N,N-dimethylformamide, N,N-dimethylacetamide, and N-methyl-2-pyrrolidone; and halogenated aliphatic hydrocarbons such as methylene chloride and dichloroethane. These reaction solvents may be used solely or as a mixture of two or more of them.

Use Amount of the Reaction Solvent:

Use amount of the foregoing reaction solvent is preferably in the range of 0.05 to 100 g, or more preferably in the range of 0.1 to 20 g, relative to 1 g of tetrahydrofurfuryl alcohol of the present invention.

Reaction Conditions

Reaction Method:

The reaction method (manufacturing equipment and manufacturing apparatus) of the present invention may be any of a batch method, a semi-batch method, and a continuous method; and any of a liquid phase slurry reaction equipment, a liquid phase fixed-bed reaction equipment, and a gas phase fixed-bed reaction equipment may be used for the reaction; however, a liquid phase slurry reaction equipment is preferably used.

Reaction Temperature and Reaction Pressure:

Reaction temperature in the reaction of the present invention is preferably in the range of 25 to 450° C., more preferably in the range of 150 to 400° C., or still more preferably in the range of 200 to 350° C. Meanwhile, the reaction of the present invention is carried out under the hydrogen pressure; and thus, the reaction pressure is in the same range as those of the before-mentioned hydrogen pressure.

Reaction Time:

Reaction time in the present invention is dependent on the reaction temperature, the reaction pressure, the concentration of the substrate (concentration of tetrahydrofurfuryl alcohol), use amount of the copper-containing catalyst, the reaction equipment, and the like; and thus, the reaction time is not particularly limited. However, in the reaction of the present invention, if the reaction time is prolonged, the conversion rate thereof can be increased, but on the contrary, products of consecutive reactions as well as decomposition products tend to increase commensurately; and thus, the reaction time is preferably in the range of 0.5 to 14 hours.

Adjustment of the Reaction Solution Composition:

The reaction in the step (I) of the present invention is stopped when conversion rate of tetrahydrofurfuryl alcohol, the manufacturing raw material, reaches 1 to 80%, preferably 5 to 75%, or more preferably 10 to 70% (this conversion rate is calculated by the later-mentioned equation (A)).

In the reaction of the step (I) of the present invention, by-production of 1-pentanol, the amount of which is the largest among the impurities in this reaction, can be suppressed to as low level as possible by carrying out the reaction of the present invention under the afore-mentioned conditions including reaction temperature, reaction pressure, reaction time, and use amount of the copper-containing catalyst. The reason why by-production of 1-pentanol needs to be suppressed to as low level as possible is because difference of boiling points between tetrahydrofurfuryl alcohol and 1-pentanol is so small that there may be a possibility of contamination of tetrahydrofurfuryl alcohol recovered in the step (II) by 1-pentanol (this step (II) will be mentioned later). If this contamination happens, 1-pentanol may be accumulated further in the reaction solution when the recovered tetrahydrofurfuryl alcohol is used in the reaction of the step (I). Here, there is a possibility that 1-pentanol accumulated in the reaction solution may be decomposed by the reaction with the copper-containing catalyst in the step (I) to give pentane, which is highly flammable with low boiling point. To safely remove this, special equipment such as, for example, a flame arrester may need to be installed in an exhausting vent; and thus, this is not economically advantageous. In addition, when amount of the by-produced 1-pentanol becomes larger, 1-pentanol may need to be separated carefully by rectification or the like during recovery of tetrahydrofurfuryl alcohol by distillation of the step (II); and thus, this is not feasible.

Step (I): Crude Reaction Product

After ending of the reaction in the step (I) of the present invention, the used copper-containing catalyst is removed from the obtained reaction solution by the operations such as, for example, filtration and decantation to obtain the crude reaction product containing the objective product 1,5-pentanediol, and by-products such as 1,2-pentanediol, 1-pentanol, 2-methyltetrahydrofurane, and tetrahydropyran, as well as tetrahydrofurfuryl alcohol, the manufacturing raw material. The crude reaction product may be used in the step (II) after work-up operations such as phase separation, extraction, and concentration, as necessary; but usually, this crude reaction product is used in the step (II) as it is. Alternatively, the step (II) may be carried out ongoingly without removing the copper-containing catalyst.

Meanwhile, this crude reaction product usually includes: 1,5-pentanediol in the range of 1 to 80% by mass and tetrahydrofurfuryl alcohol in the range of 20 to 99% by mass; preferably 1,5-pentanediol in the range of 5 to 75% by mass and tetrahydrofurfuryl alcohol in the range of 25 to 95% by mass; or more preferably 1,5-pentanediol in the range of 10 to 70% by mass and tetrahydrofurfuryl alcohol in the range of 30 to 90% by mass. If the crude reaction product having the composition ratio as mentioned above can be obtained in the step (I), recovery of tetrahydrofurfuryl alcohol may be done readily in the step (II), whereby the high-purity 1,5-pentanediol may be obtained by the operation in the step (III).

Step (I): Recovery of Copper-Containing Catalyst

After ending of the reaction in the step (I) of the present invention, the used copper-containing catalyst may be separated and recovered after ending of the reaction in the step (I) or after the step (II); however, it is preferably done after ending of the reaction in the step (I). The recovered copper-containing catalyst (recycled copper-containing catalyst) may be used again in the step (I) as it is without post-treatment or regeneration treatment. It was also confirmed in the course of the study of the step (I) of the present invention that there was no effect such as deactivation of the recycled copper-containing catalyst as compared with the fresh copper-containing catalyst to be used.

All or part of the recovered copper-containing catalyst obtained in the step (I) after the crude reaction product is separated may be reused in the next step (I). Meanwhile, the use amount of the recovered copper-containing catalyst in this case is in the range of more than 0% to 100% or less by mass relative to the total amount of the copper-containing catalyst to be used. The repeat number of the use of the recovered copper-containing catalyst is not particularly limited; however, while confirming the effect of impurities in the crude reaction product, the repeat number is usually in the range of 1 to 50 times, preferably in the range of 1 to 20 times, more preferably in the range of 1 to 10 times, or particularly preferably in the range of 1 to 5 times.

Step (II)

The step (II) of the present invention is the step in which tetrahydrofurfuryl alcohol is separated and recovered by distillation from the crude reaction product obtained in the step (I) to obtain crude 1,5-pentanediol (A), which is the raw material of the step (III).

Crude Reaction Product:

The raw material to be used in distillation of the step (II) is the crude reaction product obtained in the step (I). This crude reaction product before distillation is a mixture comprising 1 to 80% by mass of 1,5-pentanediol, the objective product, and about 0.01 to 5% by mass of impurities including 1,2-pentanediol, 1-pentanol, 2-methyltetrahydrofurane, tetrahydropyran, tetrahydropyran, and δ-valerolactone and polymer thereof (polyvalerolactones), as well as 20 to 99% by mass of tetrahydrofurfuryl alcohol, the manufacturing raw material.

<Distillation>

Distillation Method and Distillation Equipment to be Used:

The distillation method of the step (II) of the present invention may be carried out by any of a continuous method, a semi-batch method, and a batch method. The distillation equipment may be any of simple distillation equipment and distillation equipment having rectifying plates. When the distillation equipment having rectifying plates is used, number of the rectifying plates is not particularly limited. A plurality of distillation equipment may also be used. Although any of the simple distillation method and the rectification method may be used, in order to separate and recover highly pure tetrahydrofurfuryl alcohol, the rectification is preferably used. It is also allowed to carry out recovery and purification operation of tetrahydrofurfuryl alcohol by using a plurality of distillation columns.

Distillation Operation (I):

Distillation operation (I) of the present invention is the operation in which the crude 1,5-pentanediol (A) is obtained by separating and recovering tetrahydrofurfuryl alcohol and impure compounds having low boiling points from the crude reaction product obtained in the step (I).

Here, all or part of the recovered tetrahydrofurfuryl alcohol (recycle THFA) is reused in the step (I). A mixture of tetrahydrofurfuryl alcohol and low-boiling point compounds that are separated and recovered may be used in the step (I) as it is; however, if this is repeated, the low-boiling point compounds accumulate in the system thereby exerting influence to reaction results in the step (I). The low-boiling point compounds include water, 1-pentanol, and so forth; and it is known that if the recovered tetrahydrofurfuryl alcohol contains water, the catalyst activity becomes lower thereby deteriorating the reaction results. If 1-pentanol is accumulated, it undergoes hydrogenolysis to produce highly flammable pentane in the step (I); and thus, this causes the safety problem in the process. Because of these problems, it is preferable to remove water and 1-pentanol in the step (II). In this case, in order to remove only the low-boiling point compounds from the mixture of tetrahydrofurfuryl alcohol and the low-boiling point compounds, one or a plurality of distillation columns may be used.

Tetrahydrofurfuryl alcohol recovered by distillation from the crude reaction product sometimes contains valuable components such as 1,5-pentanediol and δ-valerolactone. In this case, the recovered tetrahydrofurfuryl alcohol may be used in the step (I) as it is. Alternatively, valuable components may be separated and recovered from this recovered tetrahydrofurfuryl alcohol by distillation; and these may be reused appropriately as raw materials in the steps (I) to (III).

Further, it was found as a result of the study on recovery of tetrahydrofurfuryl alcohol in the step (II) that there is no decomposition observed in tetrahydrofurfuryl alcohol during recovery thereof by distillation. Accordingly, when tetrahydrofurfuryl alcohol is recovered in the step (II) and then reused, a highly economical industrial manufacturing method can be realized.

Distillation Temperature and Distillation Pressure:

In the case that tetrahydrofurfuryl alcohol, the low-boiling point compounds, and the like are removed in the distillation operation (I), the distillation equipment may be any equipment regardless of simple distillation and rectification; but the removal is done preferably by rectification. The distillation method may be any of a continuous method, a semi-batch method, and a batch method. The distillation temperature in the distillation operation (I) is appropriately determined by respective components in the crude product before the distillation, while it is preferably in the range of 50 to 180° C., more preferably in the range of 60 to 170° C., still more preferably in the range of 70 to 150° C., or particularly preferably in the range of 80 to 130° C. The distillation pressure is not particularly limited because it is dependent on the kinds and the amounts of the low-boiling point impurities contained therein; however, for example, it is preferably in the range of 5 to 1100 hPa, more preferably in the range of 20 to 800 hPa, or particularly preferably in the range of 50 to 500 hPa.

Step (III)

Step (III) of the present invention is the step of obtaining the high-purity 1,5-pentanediol by purifying the crude 1,5-pentanediol (A) obtained in the step (II).

As to the distillation method in the step (III), any of a continuous method, a semi-batch method, and a batch-method may be used. As to the distillation equipment, any of simple distillation equipment and distillation equipment having rectifying column. In the case when the distillation equipment having rectifying column is used, number of the rectifying plates thereof is not particularly limited. In addition, a plurality of distillation equipment may be used.

Object of the step (III) is to obtain the high-purity 1,5-pentanediol by removing the high-boiling point compounds and the low-boiling point compounds from the crude 1,5-pentanediol (A); and thus, the operation method thereof is not particularly limited as far as this object can be achieved.

Step (III) has an object to obtain the high-purity 1,5-pentanediol by removing the low-boiling point compounds, the medium-boiling point compounds, and the high-boiling point compounds from the crude 1,5-pentanediol (A). The low-boiling point compounds in the step (III) are those compounds having lower boiling points than 1,5-pentanediol. The medium-boiling point compounds are those obtained after the high-boiling point compounds are removed from the compounds having higher boiling points than 1,5-pentanediol. The high-boiling point compounds are polyvalerolactones and carboxylate salts.

Distillation operation in the step (III) comprises the distillation operation (II) to remove the high-boiling point compounds from the crude 1,5-pentanediol (A) obtained in the step (II) and the distillation operation (III) to remove the low-boiling point compounds and the medium-boiling point compounds. There is no restriction as to the execution order of the distillation operation (II) and the distillation operation (III); however, it is preferable that the distillation operation (III) be executed after the distillation operation (II). The distillation operation (II) and the distillation operation (III) may be executed with plurality of numbers, respectively. However, in the case that the high-boiling point compounds are removed before the step (III), or that δ-valerolactone is allowed to contaminate the high-purity 1,5-pentanediol as the product, the distillation operation (II) may be omitted.

Example of the distillation operation in the step (III) in the case that the crude 1,5-pentanediol (A) contains the high-boiling point compounds will be explained (see FIG. 1); however, the present invention is not limited by this.

In the case that the crude 1,5-pentanediol (A) contains the high-boiling point compounds, firstly, the distillation operation (II) is carried out to remove the high-boiling point compounds as the distillation residue from the crude 1,5-pentanediol (A) to obtain crude 1,5-pentanediol.

Next, by carrying out the distillation operation (III) to remove the low-boiling point compounds and the medium-boiling point compounds from the crude 1,5-pentanediol having the high-boiling point compounds removed therefrom, and whereby the high-purity 1,5-pentanediol can be obtained. The low-boiling point compounds are removed as the distilled fraction; and the medium-boiling point compounds are removed as the distilled fraction or as the distillation residue. Usually, the high-purity 1,5-pentanediol can be obtained by this operation; however, to obtain 1,5-pentanediol having further higher purity, any one of the distillation operation (II) and the distillation operation (III) or both may be done further.

The reason why the distillation operation (II) is done at first in the case that the crude 1,5-pentanediol (A) which contains the high-boiling point compounds is purified in the step (III) is as following. This is because if the distillation operation (III) is carried out without removing the high-boiling point compounds from the crude 1,5-pentanediol, decomposition of polyvalerolactones and carboxylate salts takes place to generate δ-valerolactone so that 1,5-pentanediol and δ-valerolactone may not be separated. Another reason for this is because 1,5-pentanediol decomposes if the distillation operation (III) is carried out in the presence of the carboxylate salts.

Meanwhile, the polyvalerolactones in the present invention are the compounds belonging to the group shown by the following formula (1); and the carboxylate salts are the compounds such as those shown by the following formula (2).

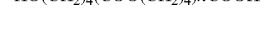

Formula (1)

$$HO(CH_2)_4(COO(CH_2)_4)_nCOOH$$

$$(n \geq 1)$$

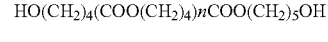

$$HO(CH_2)_4(COO(CH_2)_4)_nCOO(CH_2)_5OH$$

$$(n \geq 0)$$

-continued

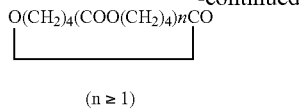

(n ≥ 1)

(In the formula, "n" represents degree of polymerization.)

$$HO(CH_2)_4[COO(CH_2)_4]_nCOOM (n≥1) \quad \text{Formula (2):}$$

(In the formula, "n" represents degree of polymerization and M represents a metal atom of the saponification agent, respectively.)

The low-boiling point compounds in the step (III) are those compounds having lower boiling points than 1,5-pentanediol; and example thereof includes water, tetrahydrofuran, 1-pentanol, tetrahydrofurfuryl alcohol, and δ-valerolactone. The medium-boiling point compounds are those having the later-mentioned high-boiling point compounds removed from the group of the compounds having higher boiling points than 1,5-pentanediol; and example thereof includes tetrahydrofurfuryl 5-hydroxypentanoate and 5-hydroxypentyl 5-hydroxypentanoate. The high-boiling point compounds are the polyvalerolactones and the afore-mentioned carboxylate salts.

Because the distillation residue removed in the distillation operation (II) of the step (III) contains, in addition to the high-boiling point compounds, valuable components including 1,5-pentanediol and the polyvalerolactones; and thus, all or part of them may be optionally reused as the raw materials for the step (I), the step (II), and the step (III). In addition, the valuable components including 1,5-pentanediol and δ-valerolactone may be recovered by distillation or the like from the distillation residue, and these respective valuable components may be optionally reused as the raw materials for the step (I), the step (II), and the step (III).

Because the distilled fraction containing the low-boiling point compounds removed in the distillation operation (III) in the step (III) contains valuable components including 1,5-pentanediol and δ-valerolactone; and thus, all or part of this fraction may be optionally reused as the raw materials for the step (I), the step (II), and the step (III). In addition, the valuable components including 1,5-pentanediol and δ-valerolactone may be recovered by distillation or the like from the distilled fraction which contains the low-boiling point compounds, and these respective valuable components may be optionally reused as the raw materials for the step (I), the step (II), and the step (III).

Because the distilled fraction containing the medium-boiling point compounds removed or the distillation residue in the distillation operation (III) in the step (II) similarly contains valuable components including 1,5-pentanediol and δ-valerolactone; and thus, all or part of this faction or the distillation residue may be optionally reused as the raw materials for the step (I), the step (II), and the step (III). In addition, the valuable components including 1,5-pentanediol and δ-valerolactone may be recovered by distillation or the like from the distilled fraction which contains the medium-boiling point compounds, and these may be optionally reused as the raw materials for the step (I), the step (II), and the step (III).

In the distillation operation (II) and/or (III) of the present invention, any of the simple distillation equipment and the rectification column may be used. When the rectification distillation is carried out, usually used distillation equipment such as the shelf-type rectifying distillation column and the packed-type rectification distillation column may be used, wherein number of the column and number of distillation are not particularly limited. As to the distillation method of the distillation operations (I) to (III) of the present invention, any of the batch method, the semi-continuous method, and the continuous method may be used. Material of construction of the distillation equipment is not particularly limited; however, in the final purification process, the distillation equipment made of stainless steel, hastelloy, or carbon steel is preferably used.

When the distillation operation (II) is carried out by using the crude 1,5-pentanediol (A) which contains the high-boiling point compounds, the distillation method and the distillation equipment used therein are not particularly limited. However, in order to suppress decomposition of the high-boiling point compounds thereby suppressing generation of δ-valerolactone in the distillation operation (II), it is preferable that the crude 1,5-pentanediol experience thermal history as little as possible. Accordingly, the distillation equipment used in the distillation operation (II) is preferably the simple distillation equipment rather than the rectification distillation column. Furthermore, the continuous distillation equipment is more preferably used than the batch or the semi-batch distillation equipment.

In the case that rectification distillation is used in the distillation operation (II) and/or (III), actual number of the plates in the distillation column to be used is preferably in the range of 1 to 100 plates, more preferably in the range of 2 to 50 plates, or particularly preferably in the range of 3 to 20 plates. The reflux ratio may be appropriately determined by confirming the separation state of each rectifying column; however, if the actual number of the plates is within the above-mentioned range, the high-purity 1,5-pentanediol can be obtained with satisfactory separation efficiency and distillation efficiency.

In the case that the distillation operation (II) and/or (III) is carried out by the rectification distillation, the reflux ratio (reflux amount/distillation amount) is preferably in the range of 0 to 50, more preferably in the range of 0.1 to 30, or particularly preferably in the range of 0.5 to 10. Excessively high reflux ratio requires long heating time; however, the reflux ratio within the above-mentioned range can give the high-purity 1,5-pentanediol with satisfactory separation efficiency and distillation efficiency.

In the case that the distillation operation (II) and/or (III) of the rectification distillation is carried out by using the packed-type rectification distillation column, kind of the packing material is not particularly limited. However, 1,5-pentanediol tends to decompose more readily as the distillation temperature becomes higher, and moreover, this is a highly viscous liquid thereby leading to large pressure difference during distillation; and thus, it is preferable to use a regular packing material so that pressure difference between the column top and the column bottom of the rectification distillation column may be small whereby keeping temperature of the distillation still not too high.

Example of the usable regular packing material includes Sulzer Packing (metal mesh mold type, manufactured by Sulzer Chemtech Ltd.), Mellapak (porous metal sheet mold type), Gempak (manufactured by Koch-Glitsch, LP), Montz-Pak (manufactured by Montz GmbH), Good Roll Packing (manufactured by Nippon Filcon Co., Ltd.), Honeycomb Pack (manufactured by NGK Insulators, Ltd.), Impulse Packing (manufactured by Nagaoka International Corp.), MC Pack (metal mesh mold type or metal sheet mold type), and Technopack. As to the materials of construction of the rectification column and of the packing material, those used in usual distillation such as, for example, stainless steel, hastelloy, ceramics, and resin may be used.

Distillation Temperature and Distillation Pressure:

Distillation temperatures in distillations in the distillation operation (II) and the distillation operation (III) may be determined appropriately by the composition of the crude product before the respective distillations; however, they are usually in the range of 40 to 300° C., preferably in the range of 50 to 250° C., more preferably in the range of 60 to 170° C., still more preferably in the range of 70 to 150° C., or particularly preferably in the range of 80 to 130° C. The distillation pressures thereat may be any of pressurized, normal, and reduced pressures; however, they are preferably 1100 hPa or less, more preferably 70 hPa or lower, still more preferably 30 hPa or lower, or particularly preferably 20 hPa or lower. Meanwhile, in these distillation operations, the distillations mentioned above may also be carried out repeatedly for two or more times in order to enhance the purity further.

<Saponification Operation>

During the study of the manufacturing process of the present invention, the inventors confirmed that there existed lactone compounds such as polyvalerolactones and δ-valerolactone as impurities in the crude reaction product obtained in the step (I), and that these mixed into the purification process of 1,5-pentanediol by distillation in the step of (II) and the step of (III) thereby decreasing purity thereof. As the specific example thereof, it was found that in the case that crude 1,5-pentanediol after completion of the step (II) was contaminated with polyvalerolactones, δ-valerolactone, the monomer produced by decomposition of polyvalerolactones, was by-produced during the distillation operation in the step (III) thereby contaminating 1,5-pentanediol.

Here, if 1,5-pentanediol contaminated with this δ-valerolactone is used in manufacturing of a polyester resin, the objective polyester resin is contaminated with this substance thereby causing a problem. Similarly, for example, if used in manufacturing of a polyurethane resin, there is a risk that a decomposition product of δ-valerolactone may deactivate the catalyst to cause a problem; and thus, in order to obtain 1,5-pentanediol suitable as raw materials for industrial resins, it is required that 1,5-pentanediol do not contain this impurity or the content thereof be extremely small if any.

Therefore, in the present invention, saponification operation may be carried out by using a saponification agent after the step (I) and/or the step (II).

The saponification operation of the present invention is incorporated into the manufacturing method of the present invention as the saponification operation (i) or the saponification operation (ii) as shown below.

Figure 2:
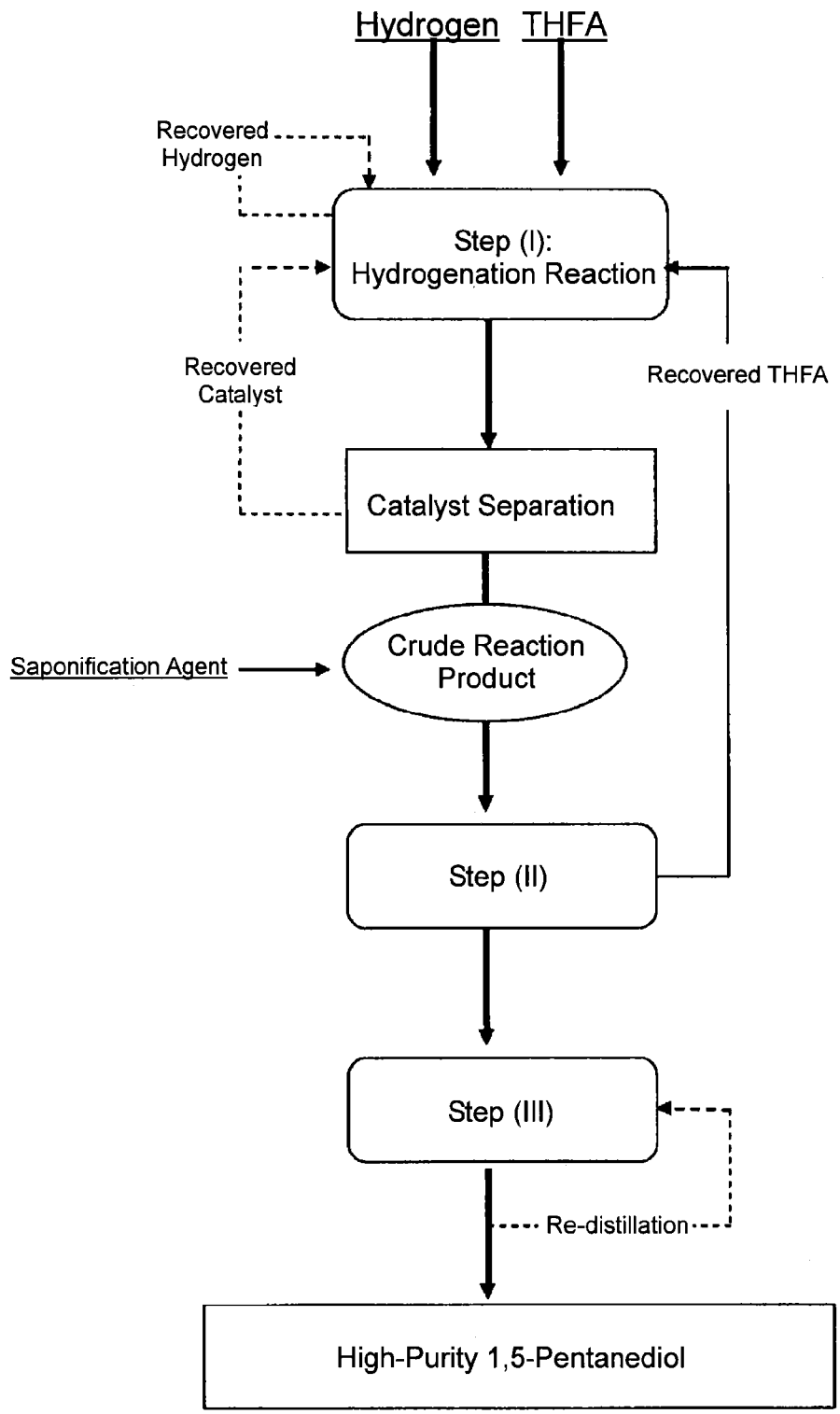
FIG. 2 shows the production scheme of the present invention in which a saponification agent is used after the step (I). Meanwhile, the respective parts shown by the dotted lines are optional operations.

Method for Manufacturing High-Purity 1,5-Pentanediol by Using the Saponification Operation (i):

In this manufacturing method, a saponification agent is added into the crude reaction product obtained in the step (I); the mixture thereby obtained is distilled in the step (II) to obtain the residue containing the crude 1,5-pentanediol (A) in the distillation still of the step (II); and then, by using this residue in the step (III), the high-purity 1,5-pentanediol is obtained (FIG. 2). Here, the saponification agent may be used as it is or as an aqueous solution thereof; however, in the saponification operation (i) of the present invention, use of the aqueous solution of the saponification agent is preferable because the afore-mentioned carboxylate salts, tetrahydrofurfuryl alcohol, and 1,5-pentanediol can be separated satisfactorily in the presence of water. In addition, the saponification agent is separated from the still residue as a solid or as an aqueous solution thereof after the operation such as filtration, decantation, and phase separation and extraction to obtain the saponification-treated product (i); and then, this may be used in the step (III). In this case, the organic solvent to be used in the phase separation and extraction is not particularly limited provided that this does not react with 1,5-pentanediol.

Figure 3:
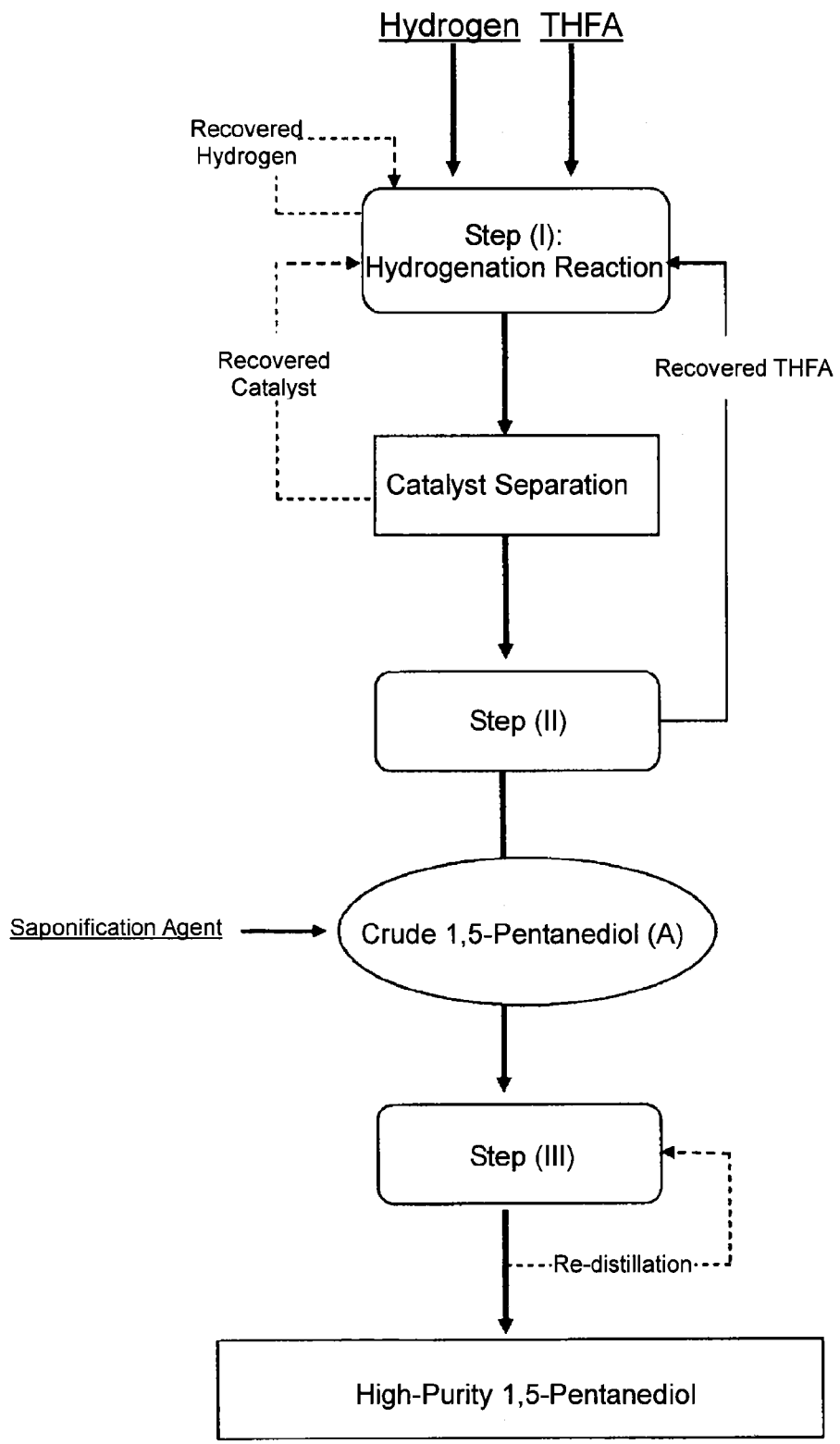
FIG. 3 shows the production scheme of the present invention in which a saponification agent is used after the step (II). Meanwhile, the respective parts shown by the dotted lines are optional operations.

Method for Manufacturing High-Purity 1,5-Pentanediol by Using the Saponification Operation (ii):

In this manufacturing method, a saponification agent is added into the crude 1,5-pentanediol (A) obtained in the step (II); and then, the mixture thereby obtained is distilled in the step (III) to obtain the high-purity 1,5-pentanediol (FIG. 3).

Method for Manufacturing the High-Purity 1,5-Pentanediol by Using the Saponification Operation (iii):

In this manufacturing method, a saponification agent is added into the crude reaction product obtained in the step (I) or into the crude 1,5-pentanediol (A) obtained in the step (II); the mixture thereby prepared is stirred or the like at normal temperature or under heating to decompose the before-mentioned lactone compounds to the carboxylate salts; and then, after completion of the decomposition, this mixture is subjected to the operation such as, for example, filtration, decantation, and phase separation and extraction to obtain the saponification-treated product after separation of the saponification agent as a solid or as an aqueous solution thereof. Then, the saponification-treated product (iii) thereby obtained is distilled in the step (II) or the step (III) to obtain the crude 1,5-pentanediol or the high-purity 1,5-pentanediol. Meanwhile, if phase separation and extraction are carried out, the organic solvent to be used therein is not particularly limited provided that this does not react with 1,5-pentanediol.

Further, a mixture of 1,5-pentanediol, tetrahydrofurfuryl alcohol, and the high-boiling point compounds including the carboxylate salts may be used optionally as the raw materials for the step (II) and the step (III).

The saponification agent to be used in the present invention is not particularly limited provided that it is a basic metal compound. Therefore, example of the saponification agent of the present invention includes hydroxides of alkaline metals such as lithium hydroxide, sodium hydroxide, and potassium hydroxide; hydroxides of alkaline earth metals such as magnesium hydroxide and calcium hydroxide; carbonate salts of alkaline metals such as lithium carbonate, sodium carbonate, potassium carbonate, and cesium carbonate; carbonate salts of alkaline earth metals such as magnesium carbonate and calcium carbonate; bicarbonate salts of alkaline metals such as lithium bicarbonate, sodium bicarbonate, and potassium bicarbonate; phosphate salts of alkaline metals such as lithium phosphate, sodium phosphate, potassium phosphate, and cesium phosphate; phosphate salts of alkaline earth metals such as magnesium phosphate and calcium phosphate; and hydrogen phosphate salts of alkaline metals such as lithium hydrogen phosphate, sodium hydrogen phosphate, and potassium hydrogen phosphate. In addition, these saponification agents may be used solely or as a mixture of two or more of them. Furthermore, the saponification agent of the present invention may be used as it is or as an aqueous solution thereof; and in addition, the saponification operation may be done in any of a homogeneous reaction system or an inhomogeneous reaction system. Use amount of the saponification agent is not particularly limited, provided that when the saponification agent is added to the afore-mentioned crude reaction product or to the crude 1,5-pentanediol (A), pH of the resulting mixture is 7.5 or higher.

In the present invention, by utilizing the saponification operation like this, polyvalerolactones, which are problematic as the impurities contained therein, were decomposed to the non-volatile carboxylate salts; and by removing these carboxylate salts, the high-purity 1,5-pentanediol of the present invention could be obtained successfully.

High-Purity 1,5-pentanediol

As discussed above, the high-purity 1,5-pentanediol obtained by the production method of the present invention is the high-purity 1,5-pentanediol with the purity thereof being usually 98% or more by mass, or preferably 98.5% or more by mass; content of the diol impurities having a secondary hydroxide group is preferably 1% or less, more preferably 0.5% or less, or still more preferably 0.3% or less; content of δ-valerolactone is preferably 1% or less, more preferably 0.3% or less, or still more preferably 0.1% or less. The high-purity 1,5-pentanediol obtained by the present invention does not contain, for example, the impurities that cause decrease in the polymerization reaction rate during polymerization of polyurethane; and thus, this is especially useful as the raw material for a soft segment of a polycarbonate diol, a polyester polyol, and the like, or as the raw material for a polyurethane resin, a polyester resin, and the like as a chain-elongating agent as it is.

EXAMPLES

Next, the present invention will be explained specifically by showing Examples; but the present invention is not limited by these Examples.

Further, in the present Examples and Comparative Examples, all of qualitative and quantitative analyses of the consumed amount of the raw material tetrahydrofurfuryl alcohol, the produced amount of the product 1,5-pentanediol, and so forth were made with a gas chromatography (GC) by using GC-2010 (manufactured by Shimadzu Corp., GC column: InertCap WAX 30 m×0.53 mm, GC detector: FID, internal standard materials: any of dimethyl glutarate, 1-octanol, and triethylene glycol was used). Meanwhile, the reaction conversion rate of the raw material tetrahydrofurfuryl alcohol, the reaction selectivity to the intended product 1,5-pentanediol, and the reaction yield thereof each was calculated by using the following equations (A) to (C). The selectivities to the respective impurities were calculated by substituting 1,5-pentanediol of the present invention to the respective impurities in the equation (B).

[Math. 1]

$$\text{Reaction conversion rate of tetrahydrofurfuryl alcohol } (\%) = \frac{[\text{consumption of tetrahydrofurfuryl alcohol (mole)}]^{*1}}{[\text{use amount of tetrahydrofurfuryl alcohol (mole)}]} \times 100(\%) \quad \text{Equation (A)}$$

*1 By quantitative analysis (GC), the above-mentioned consumption or use amount was calculated in terms of mole.

[Math. 2]

$$\text{Reaction selectivity to 1,5-pentanediol } (\%) = \frac{[\text{produced amount of 1,5-pentanediol (mole)}]^{*1}}{[\text{consumption of tetrahydrofurfuryl alcohol (mole)}]} \times 100(\%) \quad \text{Equation (B)}$$

*1 By quantitative analysis (GC), the above-mentioned consumption or use amount was calculated in terms of mole.

[Math. 3]

$$\text{Reaction yield of 1,5-pentanediol } (\%) = \frac{\text{reaction conversion rate of tetrahydrofurfuryl alcohol } (\%) \times \text{reaction selectivity to 1,5-pentanediol}(\%)}{100(\%)} \quad \text{Equation (C)}$$

Here, in the step (I) of the present invention, as calculated by using the equations (A) to (C), the reaction condition to give 80% or more as the reaction selectivity to 1,5-pentanediol, 6% or less as the reaction selectivity to 1-pentanol, and 1% or less as the reaction selectivity to 1,2-pentanediol is considered preferable because of recyclability of the recovered substances and improvement in reactivity as compared with conventional methods.

Preparation Methods of Copper-Containing Catalysts

Reference Example 1

Copper-Containing Catalyst: Copper-Zinc Catalyst

An aqueous metal salt solution was prepared by dissolving 48.6 g of cupric (II) nitrate trihydrate (12.8 g as copper) and 58.2 g of zinc (II) nitrate hexahydrate (12.8 g as zinc) into 130.3 g of deionized water. Separately, 63.3 g of sodium carbonate (anhydrous) was dissolved into 261.8 g of deionized water to prepare a basic aqueous solution. Further separately, 160.9 g of deionized water whose temperature was adjusted at 75 to 85° C. was arranged in a vessel equipped with a stirring blade, a thermometer, and a pH electrode; and then, into this solution were dropped the aqueous metal salt solution and the basic aqueous solution at the same time while keeping the formed mixture solution at pH of 7.0 to 7.5 and the temperature of 75 to 85° C. During this gradual addition, material having a pale green color was precipitated. After ending of the reaction, the precipitated material was collected by filtration, and then washed with 700 mL of deionized water to obtain a wet solid. The solid thereby obtained was dried at 120° C. to obtain 41.0 g of green powders (catalyst precursor). Thereafter, 10.0 g of the powders thus obtained were burnt in an air at 350° C. for 2 hours to obtain 7.7 g of the copper-zinc as black powders.

Reference Example 2

Copper-Containing Catalyst: Copper-Zinc-Magnesium Catalyst

An aqueous metal salt solution was prepared by dissolving 46.3 g of cupric (II) nitrate trihydrate (12.1 g as copper atom), 57.2 g of zinc (II) nitrate hexahydrate (12.6 g as zinc atom), and 5.6 g of magnesium (II) nitrate hexahydrate (0.53 g as magnesium) into 129.4 g of deionized water (at this time, if some of them remains undissolved, they may be dissolved by heating). Separately, 63.5 g of sodium carbonate (anhydrous) was dissolved into 265.6 g of deionized water to prepare a basic aqueous solution. Further separately, 159.3 g of deionized water whose temperature was adjusted at 75 to 85° C. was arranged in a vessel equipped with a stirring blade, a thermometer, and a pH electrode; and then, into this solution were dropped the aqueous metal salt solution and the basic aqueous solution at the same time while keeping the formed mixture solution at pH of 7.0 to 7.5 and the temperature of 75 to 85° C. During this dropping, material having a pale green color was precipitated. After ending of the reaction, the precipitated material was collected by filtration, and then washed with 700 mL of deionized water to obtain a wet solid. The solid thereby obtained was dried at 120° C. to obtain 42.6 g of green powders (catalyst precursor). Thereafter, 20.56 g of the powders thus obtained were burnt in an air at 350° C. for 2 hours to obtain 16.0 g of the copper-zinc-magnesium catalyst as black powders.

Reference Example 3

Copper-Containing Catalyst: Copper-Zinc-Barium Catalyst

An aqueous metal salt solution was prepared by dissolving 28.9 g of cupric (II) nitrate trihydrate (7.6 g as copper atom), 34.7 g of zinc (II) nitrate hexahydrate (7.6 g as zinc atom), and 7.6 g of barium (II) nitrate (4.0 g as barium) into 259.0 g of deionized water (at this time, if some of them remains undissolved, they may be dissolved by heating). Separately, 42.74 g of sodium carbonate (anhydrous) was dissolved into 178.4 g of deionized water to prepare a basic aqueous solution. Further separately, 105.7 g of deionized water whose temperature was adjusted at 75 to 85° C. was arranged in a vessel equipped with a stirring blade, a thermometer, and a pH electrode; and then, into this solution were dropped the aqueous metal salt solution and the basic aqueous solution at the same time while keeping the formed mixture solution at pH of 7.0 to 7.5 and the temperature of 75 to 85° C. During this dropping, material having a pale green color was precipitated. After ending of the reaction, the precipitated material was collected by filtration, and then washed with 700 mL of deionized water to obtain a wet solid. The solid thereby obtained was dried at 120° C. to obtain 30.7 g of pale green powders (catalyst precursor). Thereafter, 15.1 g of the powders thus obtained were burnt in an air at 350° C. for 2 hours to obtain 12.3 g of the copper-zinc-barium catalyst as black powders.

Meanwhile, the copper-containing catalysts without item numbers in Tables 2 and 3 (these will be shown later) were prepared in the manners similar to those of Reference Examples 1 to 3; and then, they were used.

Step (I)

Example 1

Copper-Containing Catalyst: Copper-Zinc Type Copper-Containing Catalyst

Into a 100-mL autoclave were taken 20 g tetrahydrofurfuryl alcohol (0.196 mole) and 2.0 g of the copper-zinc type metal catalyst (prepared by the method described in Reference Example 1; Cu/Zn=50/50; 10% by mass relative to the use amount of tetrahydrofurfuryl alcohol); and then, after atmosphere inside the autoclave was displaced by gases, for 5 times by a nitrogen gas and then for 5 times by a hydrogen gas, the autoclave was filled with a hydrogen gas till the inner pressure thereof reached 15 MPa. Then, after the reaction temperature was made to 240 to 260° C., a hydrogen gas was charged till the inner pressure of the autoclave reached 25 MPa, and then the reaction was carried out for 7 hours. After ending of the reaction, the reaction solution was allowed to be cooled to room temperature; and then, after the autoclave was opened, the obtained reaction solution was quantitatively analyzed by a gas chromatography to find that the objective product 1,5-pentanediol was obtained with the reaction selectivity of 97.6% thereto, with 37.4% of the reaction conversion rate of tetrahydrofurfuryl alcohol (reaction yield of 36.5%).

It was found that the reaction yield of the by-produced 1-pentanol was 0.9% (reaction selectivity of 2.4%), and the reaction yield of 1,2-pentanediol was 0.05% (reaction selectivity of 0.1%). These results are shown in Table 1.

Example 2

Copper-Containing Catalyst: Copper-Zinc Type Metal Catalyst

Into a 100-mL autoclave were taken 20 g tetrahydrofurfuryl alcohol (0.196 mole) and 2.0 g of the copper-zinc type metal catalyst (prepared by the method described in Reference Example 1; metal component ratio of Cu/Zn=50/50; use amount of 10% by mass relative to tetrahydrofurfuryl alcohol); and then, after atmosphere inside the autoclave was displaced by gases, for 5 times by a nitrogen gas and then for 5 times by a hydrogen gas, the autoclave was filled with a hydrogen gas till the inner pressure thereof reached 15 MPa. Then, after the reaction temperature was made to 260 to 280° C., a hydrogen gas was charged till the inner pressure of the autoclave reached 25 MPa, and then the reaction was carried out for 5 hours. After ending of the reaction, the reaction solution was allowed to be cooled to room temperature; and then, after the autoclave was opened, the obtained reaction solution was quantitatively analyzed by a gas chromatography to find that the objective product 1,5-pentanediol was obtained with the reaction selectivity of 95.1% thereto, with 55.2% of the reaction conversion rate of tetrahydrofurfuryl alcohol (reaction yield of 52.5%).

It was found that the reaction yield of the by-produced 1-pentanol was 2.3% (reaction selectivity of 4.2%), the reaction yield of δ-valerolactone was 0.2% (reaction selectivity of 0.4%), and the reaction yield of 1,2-pentanediol was 0.03% (reaction selectivity of 0.1%). These results are shown in Table 1.

Example 3

Copper-Containing Catalyst: Copper-Zinc Type Metal Catalyst

Into a 100-mL autoclave were taken 20 g tetrahydrofurfuryl alcohol (0.196 mole) and 2.0 g of the copper-zinc type metal catalyst (prepared by the method described in Reference Example 1; metal component ratio of Cu/Zn=50/50; use amount of 10% by mass relative to tetrahydrofurfuryl alcohol); and then, after atmosphere inside the autoclave was displaced by gases, for 5 times by a nitrogen gas and then for 5 times by a hydrogen gas, the autoclave was filled with a hydrogen gas till the inner pressure thereof reached 13 MPa. Then, after the reaction temperature was made to 240 to 250° C., a hydrogen gas was charged till the inner pressure of the autoclave reached 20 MPa, and then the reaction was carried out for 7 hours. After ending of the reaction, the reaction solution was allowed to be cooled to room temperature; and then, after the autoclave was opened, the obtained reaction solution was quantitatively analyzed by a gas chromatography to find that the objective product 1,5-pentanediol was obtained with the reaction selectivity of 96.5% thereto, with 31.9% of the reaction conversion rate of tetrahydrofurfuryl alcohol (reaction yield of 30.8%).

It was found that the reaction yield of the by-produced 1-pentanol was 0.9% (reaction selectivity of 2.8%), the reaction yield of δ-valerolactone was 0.2% (reaction selectivity of 0.5%), and the reaction yield of 1,2-pentanediol was 0.04% (reaction selectivity of 0.1%). These results are shown in Table 1.

TABLE 1-1

| Example/Comparative Example | Copper-containing Catalyst | Catalyst addition amount (% by mass) | Hydrogen gas (MPa) | Reaction Temperature (° C.) | Reaction time(h) |
|---|---|---|---|---|---|
| Example 1 | Cu—Zn | 10 | 25 | 250 | 7 |
| Example 2 | Cu—Zn | 10 | 25 | 270 | 5 |
| Example 3 | Cu—Zn | 10 | 20 | 250 | 7 |

TABLE 1-2

| Example/Comparative Example | TFHA *1 Conversion rate (%) | 1,5-PDL *2 Yield (%) | 1,5-PDL *2 Selectivity (%) | 1-PeOH *3 Selectivity (%) | 1,2-PDL *4 Selectivity (%) | δ-VL *5 Selectivity (%) |
|---|---|---|---|---|---|---|
| Example 1 | 37.4 | 36.5 | 97.6 | 2.4 | 0.1 | N.D.*6 |
| Example 2 | 55.2 | 52.5 | 95.1 | 4.2 | 0.1 | 0.4 |
| Example 3 | 31.9 | 30.8 | 96.5 | 2.8 | 0.1 | 0.5 |

*1 Tetrahydrofurfuryl alcohol
*2 1,5-Pentanediol
*3 1-Pentanol
*4 1,2-Pentanediol
*5 δ-Valerolactone
*6 N.D.: Below detection limit Example 4 to Example 13

Copper-Containing Catalysts: Copper-Zinc Type Metal Catalysts and Copper-Chromium Type Metal Catalysts The procedure of Example 1 was repeated to carry out the reaction of tetrahydrofurfuryl alcohol with hydrogen in each of Example 4 to Example 13, except that 100 g of tetrahydrofurfuryl alcohol (0.979 mole) was used in a 200-mL autoclave and that the reaction conditions shown in Table 2 were used. These results are shown in Table 2. Meanwhile, the catalyst addition amount is shown in terms of the catalyst content relative to the raw material tetrahydrofurfuryl alcohol (% by mass).

TABLE 2-1

| Example/Comparative Example | Copper-containing catalyst Composition | Copper-containing catalyst Item number | Catalyst addition amount (% by mass) | Hydrogen gas (MPa) | Reaction Temperature (° C.) | Reaction time (h) |
|---|---|---|---|---|---|---|
| Example 4 | Cu—Zn | *1 | 2 | 25 | 285 | 5 |
| Example 5 | Cu—Zn | *1 | 2 | 25 | 270 | 5 |
| Example 6 | Cu—Zn | *1 | 2 | 25 | 300 | 5 |
| Example 7 | Cu—Zn | *1 | 10 | 25 | 285 | 5 |
| Example 8 | Cu—Zn | *1 | 2 | 35 | 285 | 5 |
| Example 9 | Cu—Zn | *1 | 2 | 15 | 285 | 5 |
| Example 10 | Cu—Zn | *1 | 2 | 25 | 285 | 2 |
| Example 11 | Cu—Zn | *1 | 2 | 25 | 285 | 10 |
| Example 12 | Cu—Cr | Cu-1800P*2 | 2 | 25 | 285 | 5 |
| Example 13 | Cu—Cr | Cu-1190P*2 | 2 | 25 | 285 | 5 |

*1 Prepared by the method described in Reference Example 1
*2 Manufactured by N.E. Chemcat Corp.

TABLE 2-2

| Example/Comparative Example | THFA*3 Conversion rate (%) | 1,5-PDL*4 Yield (%) | 1,5-PDL*4 Selectivity (%) | 1-PeOH*5 Selectivity (%) | 1,2-PDL*6 Selectivity (%) |
|---|---|---|---|---|---|
| Example 4 | 30.1 | 26.8 | 88.9 | 4.3 | 0.1 |
| Example 5 | 19.5 | 18.4 | 94.1 | 3.4 | 0.3 |
| Example 6 | 49.3 | 41.9 | 85.0 | 5.6 | 0.0 |
| Example 7 | 56.0 | 50.3 | 89.7 | 5.3 | 0.1 |
| Example 8 | 36.3 | 32.0 | 87.9 | 4.7 | 0.2 |
| Example 9 | 26.9 | 22.6 | 84.2 | 3.4 | 0.1 |
| Example 10 | 22.5 | 20.2 | 89.6 | 3.5 | 0.2 |
| Example 11 | 45.6 | 40.0 | 87.9 | 4.8 | 0.0 |

TABLE 2-2-continued

| Example/Comparative Example | THFA*3 Conversion rate (%) | 1,5-PDL*4 Yield (%) | 1,5-PDL*4 Selectivity (%) | 1-PeOH*5 Selectivity (%) | 1,2-PDL*6 Selectivity (%) |
|---|---|---|---|---|---|
| Example 12 | 38.6 | 34.0 | 88.0 | 3.9 | 1.4 |
| Example 13 | 40.5 | 35.1 | 86.6 | 3.5 | 0.9 |

*3 Tetrahydrofurfuryl alcohol
*4 1,5-Pentanediol
*5 1-Pentanol
*6 1,2-Pentanediol Example 14 to Example 21

Synthesis of 1,5-pentanediol

The procedure of Example 1 was repeated to carry out the reaction of tetrahydrofurfuryl alcohol with hydrogen in each of Example 14 to Example 21, except that 100 g of tetrahydrofurfuryl alcohol (0.979 mole) was used in a 200-mL autoclave and that the reaction conditions shown in Table 3 were used. These results are shown in Table 3. Meanwhile, those catalysts not having the item numbers were prepared according to either one of Reference Example 2 or Reference Example 3 by using respective metal nitrate salts with the kinds and blending ratios thereof being adjusted so as to obtain the respective intended catalysts. Mass ratios of the respective atoms are shown in the column describing the catalysts. The catalyst addition amount is shown in terms of the catalyst content relative to the raw material tetrahydrofurfuryl alcohol (% by mass).

TABLE 3-1

| Example/ Comparative Example | Copper-containing catalyst | | | Catalyst addition amount (% by mass) | Hydrogen gas (MPa) | Reaction Temperature (° C.) | Reaction time (h) |
|---|---|---|---|---|---|---|---|
| | Composition | Item number | Catalyst ratio (% by mass) | | | | |
| Example 14 | Cu—Zn—Ba | *1 | 40/40/20 | 2 | 25 | 285 | 5 |
| Example 15 | Cu—Zn—La | *1 | 45/45/10 | 2 | 25 | 285 | 5 |
| Example 16 | Cu—Zn—Ba—La | *1 | 47/47/3/3 | 2 | 25 | 285 | 5 |
| Example 17 | Cu—Cr—Ba | *2 | — | 2 | 25 | 285 | 5 |
| Example 18 | Cu—Cr—Mn—Ba | N203SD*3 | — | 2 | 25 | 285 | 5 |
| Example 19 | Cu—Al—Mn | T-8706*4 | — | 2 | 25 | 285 | 5 |
| Example 20 | Cu—Si—Ca | Cu-0860E*5 | — | 2 | 25 | 285 | 5 |
| Example 21 | Cu—Cr—Ba | *2 | — | 10 | 25 | 300 | 6 |

*1: Prepared by the method described in Reference Example 1 or in Reference Example 2.
*2: Prepared by the method described in Journal of the American Chemical Society, 72, p. 2626 (1950).
*3: Manufactured by JGC Catalysts and Chemicals, Ltd.
*4: Manufactured by Sud-Chemie AG.
*5: Manufactured by N.E. Chemcat Corp.

TABLE 3-2

| Example/ Comparative Example | THFA*6 Conversion rate (%) | 1,5-PDL*7 Yield (%) | 1,5-PDL*7 Selectivity (%) | 1-PeOH*8 Selectivity (%) | 1,2-PDL*9 Selectivity (%) |
|---|---|---|---|---|---|
| Example 14 | 41.3 | 38.5 | 93.1 | 2.1 | 0.0 |
| Example 15 | 53.4 | 47.1 | 88.1 | 1.3 | 0.0 |
| Example 16 | 64.8 | 56.5 | 87.1 | 1.1 | 0.0 |
| Example 17 | 46.9 | 41.7 | 88.9 | 4.8 | 1.1 |
| Example 18 | 43.2 | 38.6 | 89.4 | 4.2 | 1.0 |
| Example 19 | 38.9 | 36.1 | 92.8 | 2.2 | 0.4 |
| Example 20 | 40.2 | 38.2 | 95.0 | 1.5 | 0.1 |
| Example 21 | 78.5 | 40.6 | 51.7 | 13.3 | 0.4 |

*6: Tetrahydrofurfuryl alcohol
*7: 1,5-Pentanediol
*8: 1-Pentanol
*9: 1,2-Pentanediol Example 22

Use of THFA Derived from Furfural

Into a 200-mL autoclave were taken 130 g of furfural (1.353 mole), 3.9 g of the copper-chromium type metal catalyst N203SD (manufactured by JGC Catalysts and Chemicals, Ltd.; 3% by mass relative to use amount of furfural); and then, after atmosphere inside the autoclave was displaced by gases, for 5 times by a nitrogen gas and then for 5 times by a hydrogen gas, the autoclave was filled with a hydrogen gas till the inner pressure thereof reached 4 MPa. Then, after the reaction temperature was made to 130° C., a hydrogen gas was charged till the inner pressure of the autoclave reached 4 MPa, and then the reaction was carried out for 4 hours. After ending of the reaction, the reaction solution was allowed to be cooled to room temperature; and then, after the autoclave was opened, the obtained reaction solution was filtrated through a 3.0-μm membrane filter to obtain 127.5 g of the filtrated solution. The reaction solution thus obtained was analyzed by a gas chromatography (internal standard method by using 1-octanol as the standard material) to find that purity of furfuryl alcohol was 99.1%. Into a 200-mL autoclave were taken 120 g of the obtained furfuryl alcohol reaction solution without purification (1.223 mole), and further 3.6 g of the nickel-aluminum type catalyst N-163A (manufactured by JGC Catalysts and Chemicals, Ltd.; 3% by mass relative to use amount of the furfuryl alcohol reaction solution); and then, after atmosphere inside the autoclave was displaced by gases, for 5 times by a nitrogen gas and then for 5 times by a hydrogen gas, the autoclave was filled with a hydrogen gas till the inner pressure thereof reached 4 MPa. Then, after the reaction temperature was made to 130° C., a hydrogen gas was charged till the inner pressure of the autoclave reached 4 MPa, and then the reaction was carried out for 7 hours. After ending of the reaction, the reaction solution was allowed to be cooled to room temperature; and then, after the autoclave was opened, the obtained reaction solution was filtrated through a 3.0-μm membrane filter to obtain 118.6 g of the filtered solution. The reaction solution thus obtained was analyzed by a gas chromatography (internal standard method by using 1-octanol as the standard material) to find that purity of tetrahydrofurfuryl alcohol was 92.9%. Tetrahydrofurfuryl alcohol thus obtained was purified by simple distillation to give the purity thereof of 98.0%. The same procedure of Example 1 was repeated to carry out the reaction to 1,5-pentanediol except that the tetrahydrofurfuryl alcohol thus obtained was used as the production raw material. After ending of the reaction, the reaction composition was analyzed by a gas chromatography (internal standard method by using 1-octanol and triethylene glycol as the standard materials) to find that the reaction conversion rate of tetrahydrofurfuryl alcohol was 31.9% and the reaction selectivity to 1,5-pentanediol was 90.5%. Reaction selectivities to 1-pentanol and 1,2-pentanediol were 5.2% and 0.2%, respectively.

Example 23

Use of the Recovered Copper-Containing Catalyst

The reaction in the step (I) of Example 7 was repeated. After ending of the reaction, all of the copper-containing catalyst recovered by filtration was used as it was without any post-treatment to carry out again the reaction of the step (I) by using 100 g of tetrahydrofurfuryl alcohol. Further, this recovery of the catalyst and the reaction of the step (I) were repeated four times in total to obtain 5 crude reaction products. Each of these 5 crude reaction products was quantitatively analyzed, respectively, by the gas chromatography (internal standard method by using 1-octanol and triethylene glycol as the internal standard materials). These results are shown in Table 4. Each of these crude reaction products were mixed and analyzed by the gas chromatography (internal standard method by using 1-octanol and triethylene glycol as the internal standard materials), showing 54.8% as the reaction conversion rate (average) of tetrahydrofurfuryl alcohol and 86.8% as the reaction selectivity (average) to 1,5-pentanediol. The reaction selectivities (average) to impurities 1-pentanol and 1,2-pentanediol were 5.4% and 0.04%, respectively.

TABLE 4

| Number of repeat | Copper-containing catalyst Composition | THFA *1 Content (% by weight) | 1,5-PDL *2 Content (% by weight) | 1-PeOH *3 Content (% by weight) |
|---|---|---|---|---|
| 1 | Fresh catalyst | 43.3 | 48.7 | 2.3 |
| 2 | Recovered-1 | 41.3 | 49.8 | 2.7 |
| 3 | Recovered-2 | 43.6 | 48.7 | 2.7 |
| 4 | Recovered-3 | 45.9 | 46.8 | 2.5 |
| 5 | Recovered-4 | 48.0 | 45.2 | 2.4 |

*1 Tetrahydrofurfuryl alcohol
*2 1,5-Pentanediol
*3 1-Pentanol

Example 24

Use of Recovered THFA

The procedure of Example 4 was repeated to carry out the reaction, except that the recovered THFA obtained by distillation in Example 24 mentioned later was used as the raw material in the step (I). After ending of the reaction, analysis of the reaction composition was carried out by using the gas chromatography (internal standard method by using 1-octanol and triethylene glycol as the standard materials), showing 36.2% as the reaction conversion rate (average) of tetrahydrofurfuryl alcohol and 88.8% as the reaction selectivity (average) to 1,5-pentanediol. The reaction selectivities (average) to impurities 1-pentanol and 1,2-pentanediol were 4.9% and 0.1%, respectively.

Example 25 and Example 26

Use of Water-Containing THFA

The procedure of Example 4 was repeated, except that tetrahydrofurfuryl alcohol containing water as shown in Table 5 was used, to carry out the reaction of tetrahydrofurfuryl alcohol with hydrogen of each of Example 25 and Example 26. These results are shown in Table 5.

[Table 5]

TABLE 5

| Example/ Comparative Example | Copper-containing catalyst Composition | THFA *1 Water content (% by mass) | THFA *1 Conversion rate (%) | 1,5-PDL *2 Yield (%) | 1,5-PDL *2 Selectivity (%) |
|---|---|---|---|---|---|
| Example 4 | Cu—Zn | 0.1 | 30.1 | 26.8 | 88.9 |
| Example 25 | Cu—Zn | 1.0 | 23.2 | 20.1 | 88.7 |
| Example 26 | Cu—Zn | 3.0 | 12.6 | 11.9 | 95.1 |

*1 Tetrahydrofurfuryl alcohol
*2 1,5-Pentanediol

Example 27 and Example 28

Use of THFA Having High Acid Value

The procedure of Example 18 was repeated, except that tetrahydrofurfuryl alcohol having each of the acid values as shown in Table 6 was used, to carry out the reaction of tetrahydrofurfuryl alcohol with hydrogen of each of Example 27 and Example 28. These results are shown in Table 6.

TABLE 6

| Example/ Comparative Example | Copper-containing catalyst Composition | Copper-containing catalyst Item number | THFA *2 Acid value (mg-KOH/g) | THFA *2 Conversion rate (%) | 1,5-PDL*3 Yield (%) | 1,5-PDL*3 Selectivity (%) | 1-PeOH *4 Selectivity (%) | 1,2-PDL*5 Selectivity (%) |
|---|---|---|---|---|---|---|---|---|
| Example 18 | Cu—Cr—Mn—Ba | N203SD *1 | 0.3 | 43.2 | 38.6 | 89.4 | 4.2 | 1.0 |
| Example 27 | Cu—Cr—Mn—Ba | N203SD *1 | 2.6 | 34.7 | 32.6 | 93.9 | 3.7 | 0.9 |
| Example 28 | Cu—Cr—Mn—Ba | N203SD *1 | 5.5 | 31.3 | 28.6 | 91.3 | 2.6 | 0.7 |

*1 Manufactured by JGC Catalysts and Chemicals, Ltd.
*2 Tetrahydrofurfuryl alcohol
*3 1,5-Pentanediol
*4 1-Pentanol
*5 1,2-Pentanediol

Step (II)

Example 29

Recovery of THFA 457.5 g of The mixed solution of the reaction solutions obtained in Example 23 (containing 335.5 g of tetrahydrofurfuryl alcohol and 4.1 g of 1-pentanol) was distilled by using a distillation column packed with 3 pieces of Sulzer Packings to separate tetrahydrofurfuryl alcohol to obtain 307.2 g of the recovered THFA (distillation recovery yield of 91.6%). From the gas chromatography analysis thereof, purity of the recovered THFA was 99.15% which contained 0.23% of 1-pentanol.

Example 30

Recovery of THFA 84.3 g of The mixed solution of the reaction solutions obtained in Example 21 (containing 17.6 g of tetrahydrofurfuryl alcohol and 7.5 g of 1-pentanol) was distilled by using a distillation column packed with 3 pieces of Sulzer Packings to separate tetrahydrofurfuryl alcohol, thereby obtaining 12.4 g of the recovered THFA (distillation recovery yield of 68.1%). From the gas chromatography analysis thereof, purity of the recovered THFA was 96.57% which contained 1.48% of 1-pentanol.

Step (III)

Example 31

Acquisition of High-Purity 1,5-Pentanediol 192.0 g of Distillation residue (still residue) obtained by the procedure similar to that of Example 29 (containing 158.1 g of 1,5-pentanediol) was distilled by simple distillation without distillation plates to obtain 185.9 g of crude 1,5-pentanediol (containing 156.0 g of 1,5-pentanediol). Then, this crude 1,5-pentanediol was purified by distillation by using the distillation column packed with 3 pieces of Sulzer Packings to obtain 134.7 g of the main fraction containing 1,5-pentanediol (distillation recovery yield of 85.6%). From the gas chromatography analysis thereof, purity of 1,5-pentanediol of the main fraction was 99.14% (area %) which contained 0.03% of 5-valerolactone. In addition, it contained 0.01% of 1,2-pentanediol and 0.09% of 1,5-hexanediol, while content of 1,4-cyclohexanediol was less than the detection limit of the gas chromatography analysis.

Example 32

Acquisition of High-Purity 1,5-Pentanediol

To the mixed solution of the reaction solutions obtained by the procedure similar to that of Example 4, Example 6, Example 7, and Example 11 (total of 500.7 g, containing 289.6 g of tetrahydrofurfuryl alcohol, 179.2 g of 1,5-pentanediol, 4.4 g of 1-pentanol, and 0.17 g of 1,2-pentanediol) was added 4.2 g of a 50% aqueous sodium hydroxide solution; and then, the resulting mixture was stirred at 80° C. for 30 minutes. Thereafter, this solution was distilled by simple distillation without distillation plates to distill out tetrahydrofurfuryl alcohol to obtain 214.2 g of the distillation residue (still residue, which contained 168.3 g of 1,5-pentanediol). Then, this distillation residue was purified by distillation by using the distillation column packed with 3 pieces of Sulzer Packings to obtain 145.7 g of the main fraction containing 1,5-pentanediol (distillation recovery yield of 85.7%). From the gas chromatography analysis thereof, purity of 1,5-pentanediol of the main fraction was 98.99% (area %) which contained 0.04% of δ-valerolactone. In addition, it contained 0.01% of 1,2-pentanediol and 0.09% of 1,5-hexanediol, while content of 1,4-cyclohexanediol was less than the detection limit of the gas chromatography analysis.

Example 33

Acquisition of High-Purity 1,5-pentanediol 1,5-Pentanediol in the distillation residue (still residue) obtained by the procedure similar to that of Example 29 (116.5 g, containing 102.1 g of 1,5-pentanediol) was purified directly by distillation by using the distillation column packed with 5 pieces of Sulzer Packings to obtain 79.1 g of the main fraction containing 1,5-pentanediol (distillation recovery yield of 75.6%). From the gas chromatography analysis thereof, purity of 1,5-pentanediol of the main fraction was 99.26% (area %) which contained 0.31% of δ-valerolactone. In addition, it contained 0.10% of 1,5-hexanediol, while contents of 1,2-pentanediol and of 1,4-cyclohexanediol were less than the detection limit of the gas chromatography analysis.

Reference Example 4

Commercially Available 1,5-pentanediol

Commercially available 1,5-pentanediol was analyzed by the gas chromatography; and it was found that purity of 1,5-pentanediol was 97.97%, containing 1.09% of 1,5-hexanediol and 0.03% of 1,4-cyclohexanediol.

INDUSTRIAL APPLICABILITY

The present invention relates to a method for producing objective high-purity 1,5-pentanediol with a high reaction selectivity thereto and with a convenient procedure by using a copper-containing catalyst which is industrially inexpensive.

1,5-Pentanediol produced by the method of the present invention is useful as a raw material (monomer) for polymers such as, for example, a polyester, a polycarbonate, and a polyurethane, and as a raw material for a pharmaceutical drug and an agricultural chemical, an additive for a resin, a cleaning solvent, and the like.

The invention claimed is:

1. A method for producing high-purity 1,5-pentanediol, the method comprising:
hydrogenolyzing tetrahydrofurfuryl alcohol with hydrogen in the presence of a copper-comprising catalyst at a reaction temperature of from 200 to 350° C. and a reaction pressure of from 1 to 40 MPa until conversion rate of tetrahydrofurfuryl alcohol reaches 80% or less, thereby obtaining a crude reaction product;
separating tetrahydrofurfuryl alcohol and crude 1,5-pentanediol (A) from the crude reaction product, thereby obtaining recovered tetrahydrofurfuryl alcohol and the crude 1,5-pentanediol (A), and then, supplying the recovered tetrahydrofurfuryl alcohol as a raw material for said hydrogenolyzing; and
distilling the crude 1,5-pentanediol (A), thereby obtaining the high-purity 1,5-pentanediol.

2. The method according to claim 1, wherein water content in the tetrahydrofurfuryl alcohol in said hydrogenolyzing is 1% or less by mass.

3. The method according to claim 1, wherein the copper-comprising catalyst after use is recovered by separation after ending of said hydrogenolyzing, thereby obtaining a recovered copper-comprising catalyst, which is reused in said hydrogenolyzing.

4. The method according to claim 1, wherein the crude 1,5-pentanediol (A) obtained in said separating is distilled to remove high-boiling point compounds, thereby obtaining a second crude 1,5-pentanediol, which is used in said distilling.

5. The method according to claim 1, wherein a saponification agent is added to the crude reaction product obtained in said hydrogenolyzing before said separating and said distilling.

6. The method according to claim 1, wherein a saponification agent is added to the crude 1,5-pentanediol (A) obtained in said separating before said distilling.

7. The method according to claim 1, wherein a total amount of diol compounds having a secondary hydroxy group contained in the high-purity 1,5-pentanediol obtained in said distilling is 1% or less by mole.

8. The method according to claim 1, wherein the copper-comprising catalyst used in said hydrogenolyzing comprises at least one atom "B" selected from the group consisting of zinc, iron, aluminum, chromium, and silicon.

9. The method according to claim 8, wherein the copper-comprising catalyst used in said hydrogenolyzing further comprises at least one atom "C" selected from the group consisting of barium, calcium, manganese, lanthanum, cerium, and magnesium.

10. The method according to claim 1, wherein the tetrahydrofurfuryl alcohol used in said hydrogenolyzing is tetrahydrofurfuryl alcohol synthesized by using furfural as a raw material.

11. The method according to claim 1, wherein acid value of the tetrahydrofurfuryl alcohol used in said hydrogenolyzing is 2 mg-KOH/g or less.

* * * * *